(12) United States Patent
Pandya et al.

(10) Patent No.: US 9,439,556 B2
(45) Date of Patent: Sep. 13, 2016

(54) INTELLIGENT AUTONOMOUS CAMERA CONTROL FOR ROBOTICS WITH MEDICAL, MILITARY, AND SPACE APPLICATIONS

(75) Inventors: Abhilash Pandya, Grosse Isle, MI (US); Michael D. Klein, Grosse Pointe, MI (US); Ajay V. Mudunuri, Farmington Hills, MI (US); Alex Cao, Columbia, SC (US); Luke Reisner, Madison Heights, MI (US); Brady King, Clinton Township, MI (US); Syed Ali, Madison Heights, MI (US)

(73) Assignee: Wayne State University, Detroit, MI (US)

( * ) Notice: Subject to any disclaimer, the term of this patent is extended or adjusted under 35 U.S.C. 154(b) by 461 days.

(21) Appl. No.: 13/992,909

(22) PCT Filed: Dec. 9, 2011

(86) PCT No.: PCT/US2011/064171
§ 371 (c)(1),
(2), (4) Date: Aug. 20, 2013

(87) PCT Pub. No.: WO2012/078989
PCT Pub. Date: Jun. 14, 2012

(65) Prior Publication Data
US 2013/0331644 A1    Dec. 12, 2013

Related U.S. Application Data

(60) Provisional application No. 61/421,877, filed on Dec. 10, 2010.

(51) Int. Cl.
*A61B 1/00* (2006.01)
*A61B 19/00* (2006.01)
*B25J 9/16* (2006.01)

(52) U.S. Cl.
CPC ....... *A61B 1/00108* (2013.01); *A61B 1/00149* (2013.01); *B25J 9/1682* (2013.01); *A61B 2019/2207* (2013.01); *G05B 2219/39114* (2013.01)

(58) Field of Classification Search
CPC .......... A61B 1/00149; A61B 19/2203; A61B 2019/2207; B25J 9/1682; B25J 9/1697
See application file for complete search history.

(56) References Cited

U.S. PATENT DOCUMENTS

| 5,820,545 A | 10/1998 | Arbter et al. | |
| 5,836,869 A * | 11/1998 | Kudo ................. | A61B 1/00039 600/102 |
| 6,036,637 A * | 3/2000 | Kudo ................. | A61B 1/00039 600/102 |

(Continued)

FOREIGN PATENT DOCUMENTS

WO    WO2009/045827 A2    4/2009

OTHER PUBLICATIONS

International Search Report for International Application No. PCT/US2011/05181, Dated Apr. 19, 2012.

*Primary Examiner* — John P Leubecker
(74) *Attorney, Agent, or Firm* — Brinks Gilson & Lione

(57) ABSTRACT

A system for autonomous camera control includes a first robot having a surgical tool mounted as an end effector and a second robot having a camera mounted as an end effector. A controller may be provided for manipulating the second robot, where the controller stores a first kinematic model for the first robot and a second kinematic model for the second robot. The controller may be configured to automatically manipulate the second robot to position the camera based on the second kinematic model and an expected position of the surgical tool according the first kinematic model of the first robot. The controller is further configured to identify a threshold angle from a viewing axis of the camera, calculate a tool angle from the viewing axis of the camera, and move the camera toward or further away from the tool depending on if the tool angle is greater than or less than the threshold angle.

18 Claims, 17 Drawing Sheets

(56) References Cited

U.S. PATENT DOCUMENTS

| | | | |
|---|---|---|---|
| 6,493,608 B1 * | 12/2002 | Niemeyer | A61B 19/22 606/130 |
| 6,671,581 B2 | 12/2003 | Niemeyer et al. | |
| 6,766,204 B2 | 7/2004 | Niemeyer et al. | |
| 6,926,709 B2 | 8/2005 | Bieger et al. | |
| 8,073,528 B2 | 12/2011 | Zhao et al. | |
| 8,108,072 B2 | 1/2012 | Zhao et al. | |
| 8,147,503 B2 | 4/2012 | Zhao et al. | |
| 8,155,479 B2 | 4/2012 | Hoffman et al. | |
| 2003/0114962 A1 * | 6/2003 | Niemeyer | A61B 19/22 700/245 |
| 2005/0273199 A1 * | 12/2005 | Ban | B25J 9/1682 700/248 |
| 2006/0258938 A1 * | 11/2006 | Hoffman | A61B 1/00193 600/424 |
| 2007/0138992 A1 * | 6/2007 | Prisco | A61B 19/22 318/568.21 |
| 2008/0221591 A1 * | 9/2008 | Farritor | A61B 17/00234 606/130 |
| 2009/0012533 A1 | 1/2009 | Barbagli et al. | |
| 2009/0088634 A1 * | 4/2009 | Zhao | B25J 9/1689 600/427 |
| 2009/0326556 A1 * | 12/2009 | Diolaiti | A61B 1/00009 606/130 |
| 2010/0164950 A1 | 7/2010 | Zhao et al. | |
| 2010/0168763 A1 | 7/2010 | Zhao et al. | |
| 2010/0331855 A1 | 12/2010 | Zhao et al. | |
| 2011/0238081 A1 | 9/2011 | Cooper et al. | |
| 2012/0221011 A1 | 8/2012 | Larkin et al. | |

\* cited by examiner

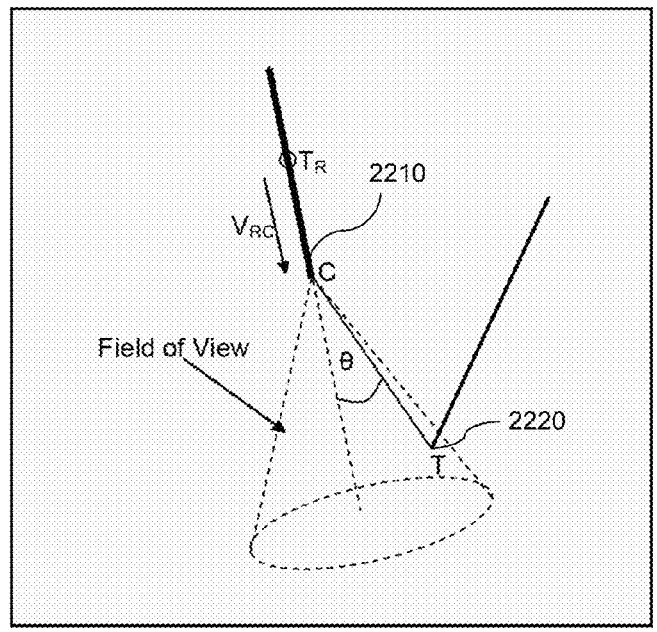
FIG. 22
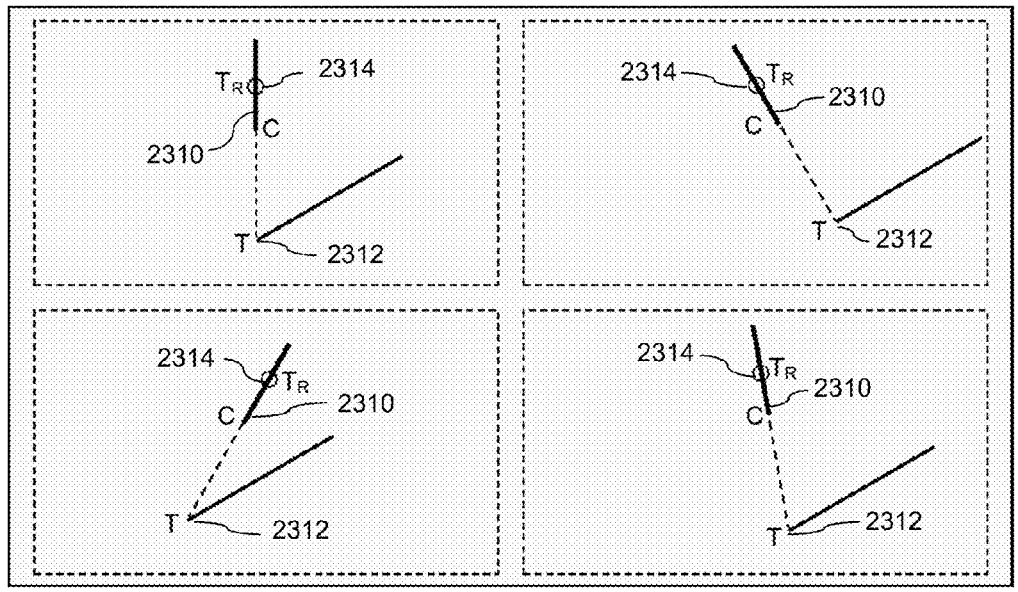
FIGS. 23a-d

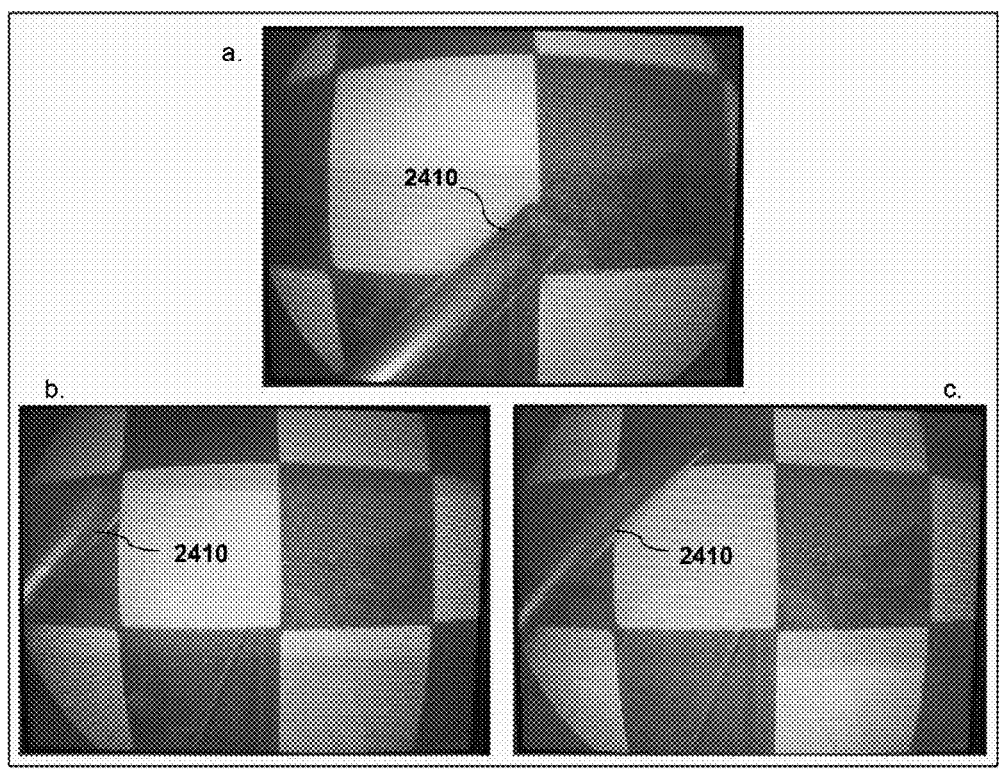
FIGS. 24a-c

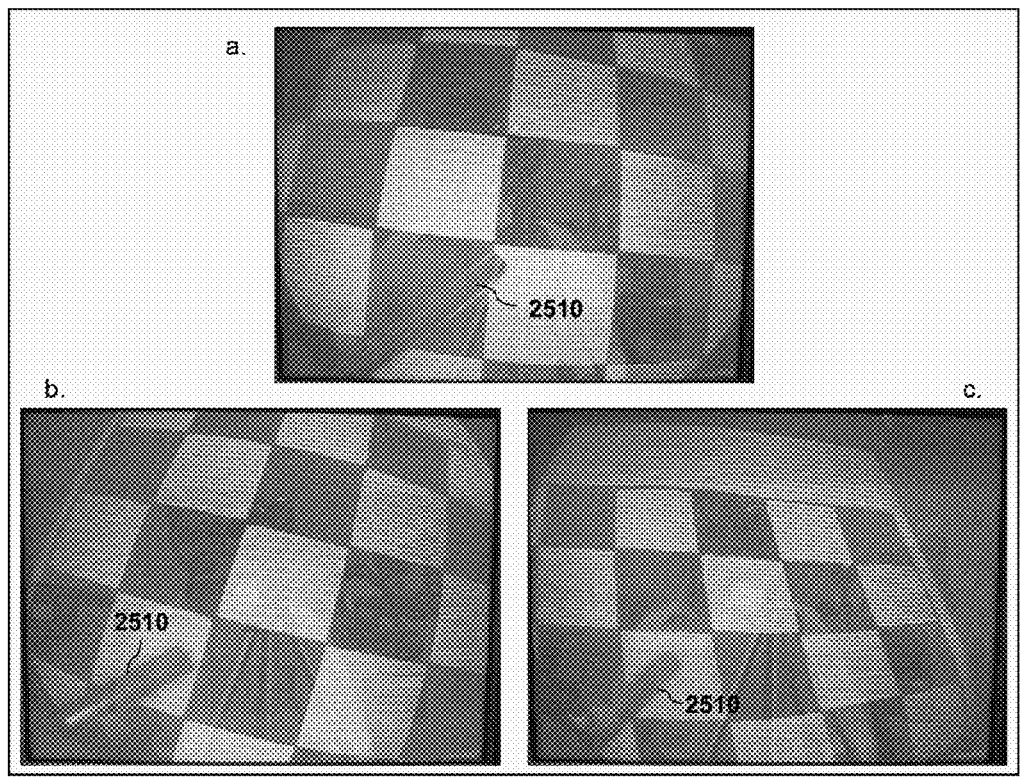
FIGS. 25a-c ately. Further, it understood that the viewing axis would

INTELLIGENT AUTONOMOUS CAMERA CONTROL FOR ROBOTICS WITH MEDICAL, MILITARY, AND SPACE APPLICATIONS

CROSS REFERENCE TO RELATED APPLICATIONS

This application is a 371 national stage application of PCT Application No. PCT/US2011/064171, filed Dec. 9, 2011, which application claims the benefit of U.S. Provisional Patent Application No. 61/421,877 filed Dec. 10, 2010, the content of which is hereby incorporated by reference in its entirety.

BACKGROUND

Field of the Invention

This application is related to a robotic system with autonomous camera control.

BRIEF DESCRIPTION OF THE DRAWINGS

FIG. 22 is a diagram showing the field of view of the camera and the tool;

FIGS. 23a-d is a diagram illustrating the different positions of the tool and the camera positioned at the calculated position;

FIGS. 24a-c are images of the camera view in autonomous zoom mode;

FIGS. 25a-c are images of the camera view in the zoom mode; and

DETAILED DESCRIPTION

Figure 1:
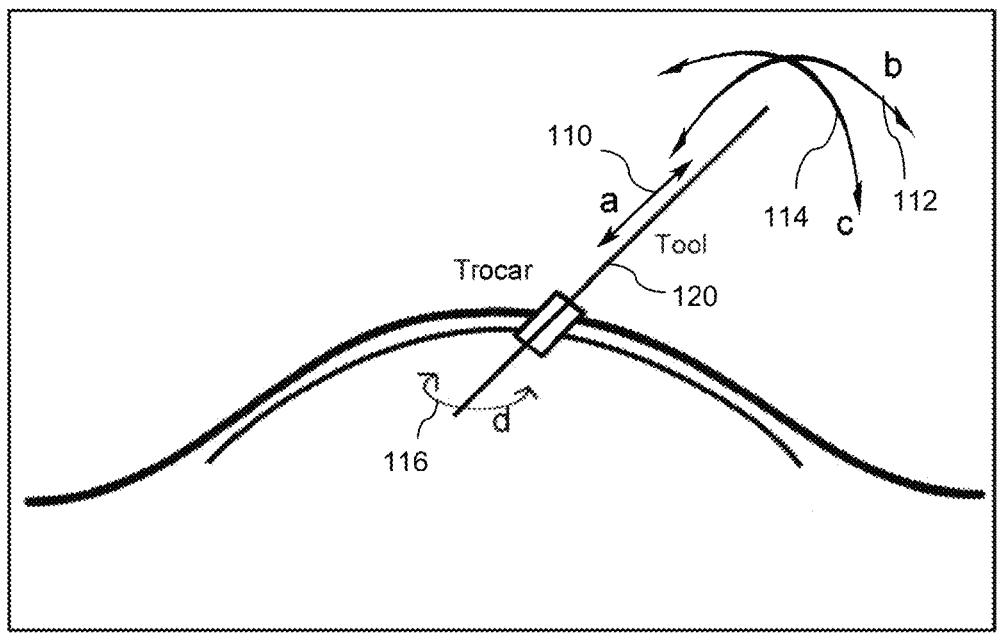
FIG. 1 is a diagram illustrating the 4 degrees of freedom of a laparoscopic tool.

A system for autonomous camera control is provided. The system may include a first robot having a surgical tool mounted as an end effector and a second robot having a camera mounted as an end effector. A controller may be provided for manipulating the second robot, where the controller stores a first kinematic model for the first robot and a second kinematic model for the second robot. The controller may be configured to automatically manipulate the second robot to position the camera based on the second kinematic model and an expected position of the surgical tool according the first kinematic model of the first robot.

The controller may be configured to identify a threshold angle from a viewing axis of the camera, calculate a tool angle from the viewing axis of the camera, moving camera further away from the tool if the tool angle is greater than the threshold angle.

The tool angle is calculated according to the relationship:

$$\theta = \cos^{-1}\left(\frac{\overrightarrow{V_{RC}} \cdot \overrightarrow{V_{CT}}}{|V_{RC}| * |V_{CT}|}\right)$$

where $V_{RC}$ is the vector between the trocar and the camera position, $V_{CT}$ is the vector between the camera and the tool, and $\theta$ is the tool angle.

The angles and threshold angles may be relative to the camera viewing axis, and distances may be calculated based on the kinematic model of the camera carrying robot and the kinematic model of the tool carrying robot. Although it is understood that other methodologies may be used including using the camera image, or external measuring devices, like trackers. Further, it understood that the viewing axis would be a line typically perpendicular to the sensing surface of the camera extending from the center of the sensing surface. However, it is also understood in the art that viewing axis may vary, for example based on the optical setup the viewing axis may be bent or transformed by the optical system.

The controller may also be configured to calculate a distance of the camera from a trocar point. As such, the controller may prevent the camera from adjusting the camera backward based on the threshold angle when the distance of the camera from the trocar point is less than a threshold distance.

The controller may be configured to identify a threshold angle from a viewing axis of the camera, calculate a tool angle from the viewing axis of the camera, moving camera closer to the surgical tool if the surgical tool angle is less than the threshold angle.

The controller also may be configured to calculate a distance of the camera from the surgical tool, the controller preventing the camera from adjusting the camera toward the surgical tool based on the threshold angle when the distance of the camera from the surgical tool is less than a threshold distance.

The controller may be in communication with an input device for control of the first robot and a display for providing an image from the camera, the system being configured to maintain the relation between the image and the input device. The relationship may be maintained by manipulating (e.g. rotating, transforming, etc.) the image or by moving the robot in response to input device based at least in part on the coordinate system of the image.

The controller may also track the roll of the camera and provide cues to the surgeon suggesting the direction of motion of the surgical tool.

The controller may also be configured to maintain a relationship between the camera and the tool based on the first and second kinematic model. Further, the controller may be configured to position the camera so that the tool is in the center of the view.

The controller may calculate a first point which is on a line between the trocar point and the surgical tool, where the first point is located a distance away from the trocar point that is about one fourth of a distance from the trocar point to the surgical tool.

The controller may position the camera based on the relationship:

$$T_{CT} = T_{AT}^{-1} * T_{AC}$$

where $T_{CT}$ is the transform from the camera to the tool, $T_{AT}$ is the transform from the origin of the second robot to the tool, $T_{AC}$ is the transform from the origin of the second robot to the camera.

The system of any of the previous claims, wherein the first robot is one robot of a plurality of robots each robot of the plurality of robots having a surgical tool of a plurality of surgical tools, and controller is configured to position the camera such that the mid-point of the plurality surgical tools is in the center of the field of view of the camera. In addition, the system may include other elements as further described throughout this specification.

In another aspect of the system, the controller is configured to define a zone such that the first robot will not be allowed to enter the zone. As such, the controller may be configured to determine the motion of the second robot to avoid entering the zone that was defined with respect to the first robot.

A method for autonomous camera control is also contemplated. The method may include, storing a first kinematic model for a first robot and a second kinematic model for a second robot, and automatically manipulating the second robot to position a camera based on the second kinematic model and an expected position of a surgical tool mounted on the first robot according the first kinematic model of the first robot.

The method may also include identifying a threshold angle from a viewing axis of the camera, calculating a tool angle from the viewing axis of the camera, moving camera further away from the tool if the tool angle is greater than the threshold angle.

The method may also include identifying a threshold angle from a viewing axis of the camera, calculating a tool angle from the viewing axis of the camera, and moving camera closer to the surgical tool if the surgical tool angle is less than the threshold angle.

The method may also include communicating with an input device for control of the first robot and a display for providing an image from the camera, and maintaining the relation between the image and the input device.

The method may also include maintaining a relationship between the camera and the tool based on the first and second kinematic model.

The method may also include calculating a first point which is on a line between the trocar point and the surgical tool, wherein the first point is located a distance away from the trocar point that is about one fourth of a distance from the trocar point to the surgical tool, and moving the camera to the first point. In addition, the method may include other elements as further described throughout this specification.

A computer readable medium containing instructions in the form of a computer program for performing the method steps or for controlling system elements as described throughout this specification is also contemplated herein.

Robots are being used to perform a wide range of surgeries. They have provided surgeons with additional features like motion scaling, tremor filtration etc. While robotics has made the surgeon's life easier in the operating room by augmenting their abilities, automation of the surgery has not yet been possible. As a first step towards automation, this project is intended to develop an autonomous camera positioning system for the existing surgical robot platforms. In some system implementations, the system may be designed to enable the surgeon to control the position of the camera without using the conventional methods, like a remote control or voice control. The surgeon should not need to worry about the camera position while doing his tasks, and the system could calculate the best position for the camera and control the position of the camera accordingly.

In this section, minimally invasive and robotic surgery is discussed, however, the system described herein could be adapted to military and space applications, as well.

Laparoscopic surgery, also known as, Minimally Invasive Surgery (MIS), is a technique where long tools are inserted into the patient's body through small incisions to perform a surgery. This allows the surgeons to perform the surgery without having to make large incisions in the patient's body. For the open procedure, the patient was opened to access the internal organs. Whereas in a laparoscopic procedure, the internal organs are accessed using long tools through small openings in the patient's abdomen.

Laparoscopic surgeries are usually performed in the abdominal area. Since the patient is not opened to access the organs, there is very little space for the surgeons to operate the tools. In order to overcome this problem, the area at which the operation is performed is filled with Carbon Dioxide ($CO_2$) to inflate the area. The laparoscopic tools, along with a laparoscopic camera, are then inserted into the patient's body.

The video from the laparoscopic camera is shown to the surgeon who operates the tools based on these images. There are a wide range of laparoscopic tools to perform different types of surgical tasks like holding, cutting, cauterizing, etc. The tools and the camera are inserted into the body through small openings called trocars. The surgeon can move the tool inside the patient's body by moving the handles on the other side of the tool, which is outside the patient's body.

MIS has many advantages over open procedures. Since the size of the incisions is much smaller when compared to those of an open surgery the patient has less pain after the surgery and less blood loss which leads to faster recovery times.

However, in MIS the surgeon is forced to operate with long instruments whose motion is highly restricted by the small opening through which it is inserted into the body.

Also, the opening through which the tools are inserted act as a pivot point and all the motions are reversed. Hence, if the surgeon has to move the tip of the tool to the left, he has to move his hand to the right. This is called the fulcrum effect. It is also possible that the amount of tremor in the surgeons hand is amplified at the tip of the tools, based on the position of the opening with respect to the tool.

In laparoscopic surgery, the camera is held by an assistant who follows the surgeon's instructions and places the camera wherever the surgeon asks. One disadvantage of the assistant holding the camera is that camera is not held by stable platform. Any tremor in the assistant's hands will lead to blurred images and fatigue will played major role in the assistant's ability to hold the camera at the same place. When comparing the performance between a robot and an assistant holding the camera during a surgery, it has been found that robot provides a stable platform and better accuracy than a surgical assistant.

Hence performing MIS is more difficult for the surgeon because of reduced dexterity, the fulcrum effect and poor ergonomic conditions. There have also been a few reports suggesting that the surgeons experience physical deformities on themselves while performing MIS over a long period of time. A study was performed on laparoscopic surgeons and found that laparoscopic surgery is more taxing on the surgeons. The report indicated that 87% of laparoscopic surgeons who perform laparoscopic surgery regularly suffer from injuries.

In order to eliminate the difficulties involved in traditional MIS, robots are being used manipulate the laparoscopic tools. Robotic surgery puts the surgeon in an ergonomically comfortable position during the surgery. It also eliminates the fulcrum effect and tremors. Robotic surgery also provides certain features like motion scaling, where the large motions of the surgeons can be scaled down to small motions of the tools, which leads to more accuracy. Robotic surgery also restores the 6 degrees of freedom at the tools, where the tools are restricted to only 4 degrees of freedom in traditional MIS.

FIG. 1 shows the 4 degrees of freedom of a laparoscopic tool 120. As shown in the figure, the 4 degrees of freedom of a laparoscopic tool are:
  a) In and Out (arrow 110).
  b) Up and Down (arrow 112).
  c) Left and Right (arrow 114).
  d) Rotation/Roll (arrow 116).

On the other hand, in robotic surgery, the degrees of freedom of the robotic tool are similar to those of the human hand. Because of this feature, the surgeons will be able to reach certain areas which were hard to reach using traditional MIS. Robotic systems also provide much more stable platform to hold the laparoscopic camera when compared to traditional laparoscopic approach, where the camera is held by an assistant.

Robotic surgery augments the strengths of the surgeon with those of the robot. Robots are tireless and accurate. They can move the surgical instruments in a defined trajectory any number of times with the same precision and accuracy. On the other hand, a surgeon is medically trained and is driven by judgment. Hence, a partnership between the surgeon and the robot can result in performing a task better than either can perform alone. Robotic surgery, currently, is performed in a master-slave environment, where the surgeon manipulates a controller remotely and the robot performs the surgery on the patient. This mode of operation is also known as teleoperation. In this master-slave environment, the robot can be controlled only by the surgeon's actions and there are no automated tasks being done. The "Zeus® Robotic Surgical System" (Intuitive Surgical Inc. Sunnyvale, Calif.) and the "da Vinci Surgical System" (Intuitive Surgical Inc. Sunnyvale, Calif.) are the most commonly used surgical robots.

Figure 2:
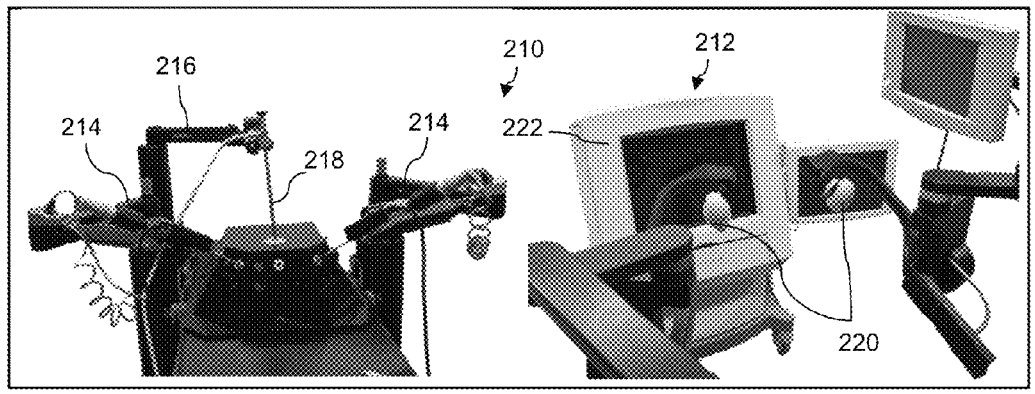
FIG. 2 is a picture of the Zeus® Robotic Surgical System.

FIG. 2 shows the Zeus® Robotic Surgical System 210, with the master controller 212 and the slave robots 214. It also shows the AESOP® Endoscope Positioner 216 (Intuitive Surgical Inc. Sunnyvale, Calif.) which holds the laparoscopic camera 218. The surgeon manipulates the two hand controllers 220 at the master controller 212 to control the surgical instruments which can be seen in the monitor 222 in front of the master controller 212.

Figure 3:
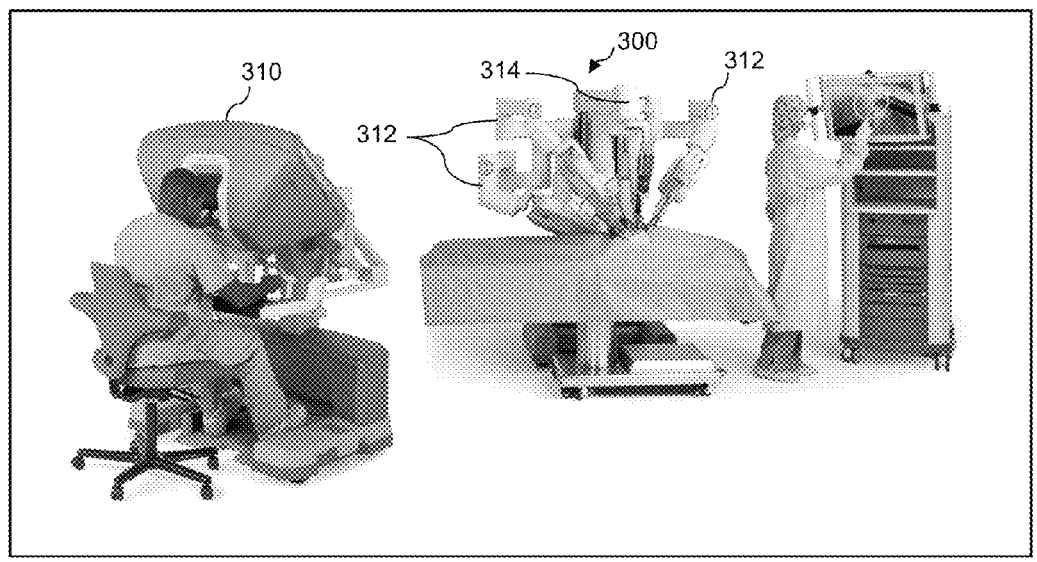
FIG. 3 is a picture of the daVinci Surgical System.

FIG. 3 shows the daVinci Surgical System 300 which is one of the most prevalent surgical robots currently. The deVinci Surgical system has a master controller 310, slave robot 312, and camera robot 314 similar to the previously described system.

Even with the advantages of robotic surgery over traditional laparoscopic procedures, there are certain tasks which the surgeons find difficult to perform, especially when they are repeated again and again. Tasks like suturing and knot tying are some of the most common tasks performed in surgery. It has been found that suturing sometimes can take more time when performed robotically when compared to that of a laparoscopic procedure. Hence automation or augmentation of these tasks within the robotic surgery environment might be desirable. In this way, repetitive tasks could be done automatically such that the surgeon's performance could be increased. This would lead towards a better partnership between the surgeon and the robot and can possibly reduce the time taken to perform these surgeries. The current systems provide only visual feedback to the surgeon and do not provide any kind of positional feedback. The current systems which are built for master-slave control only are closed architecture and do not provide the position and orientation of the operating tool tip. This positional feedback of the end-effector is necessary to perform any kind of automation using the robot. In addition, most surgeries utilize more than one surgical arm and hence a kinematic relation between each arm is highly important in order to coordinate automation between arms. For example, if the surgeon wants to define a boundary or a safe zone for the robot to maneuver, without a kinematic relationship between the robots, the surgeon is forced to define the boundaries for each robot. If a kinematic relationship between each robot is determined, then defining the boundaries with one robot would be sufficient as these boundaries can be transformed between each robot. Also a kinematic relationship between each of the robots links can be used to avoid collision between the robots.

Figure 4:
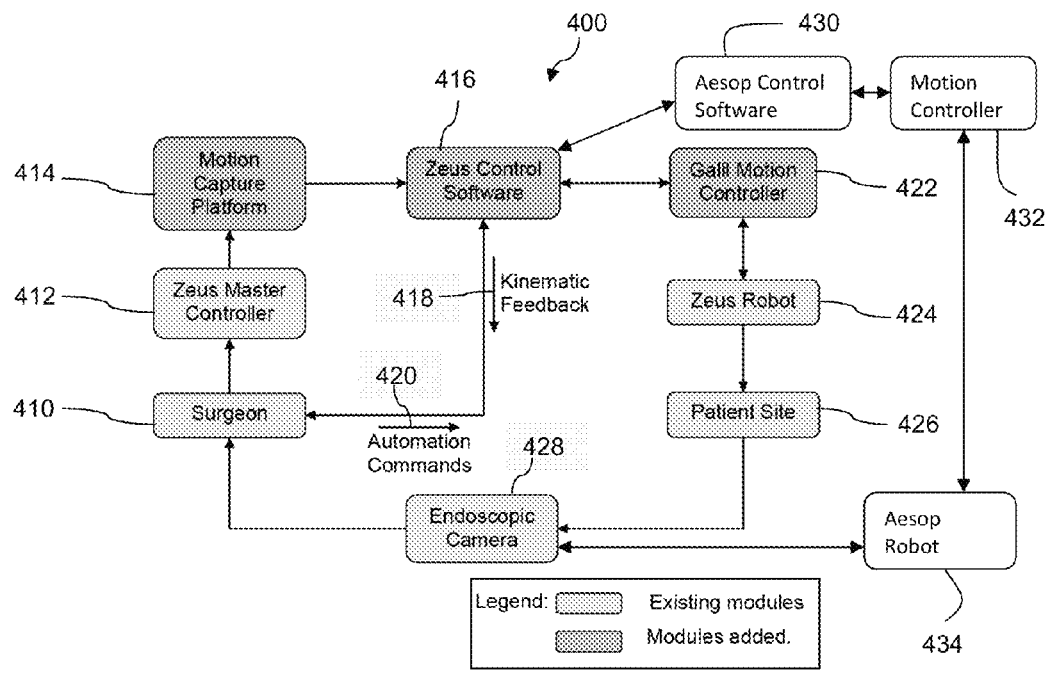
FIG. 4 is a block diagram of a surgical system with autonomous camera control.

The closed architecture of the current robotic systems do not allow for programming or research into automation. Therefore, the robotic systems may be modified to enable kinematic feedback of the surgical tools and autonomous control. FIG. 4 shows a basic block diagram of a surgical system, which allows such kinematic feedback and also automation of tasks. The surgeon 410 interacts with the master controller 412 to provide input for controlling the Zeus robot and surgical tool attached thereto. The master controller 412 may be in communication with a motion capture platform 414 to interpret the user input from the surgeon 410. The motion capture platform provides commands to the control software 416 based on the user input. The control software 416 provides kinematic feedback 418 to the surgeon, while the surgeon may provide automation commands 420 to the control software 416. The control software 416 may then provide commands to a motion controller 422. The motion controller 422 may then provide signals to the motors of the robot 424 to manipulate the robot joints according to the user input. The robot 424 using the surgical tool interacts with the patient site 426. The camera 428 simultaneously images the patient site 426 and provides visual feedback to the surgeon 410. In addition, the control software 416 for the motion of the surgical tool may be in communication with the control software 430 for the motion of the camera. The control software 430 may provide commands to the motion controller 432 for manipulating the robot 434 to position the camera 428 based on the information from the control software 416. Further it is understood that one of more of the controller, platform, or software blocks represented in FIG. 4 may be integrated into a single controller system or may work together in cooperation as separate elements which collectively and simply may be referred to as a controller elsewhere in this application.

The motion control hardware of present systems can be modified or replaced to enable kinematic feedback and automation, along with the ability to tele-operate the robot. The hardware/software interface shown in the figure can control the robot based on the signals from the master controller and also provide the user with positional feedback of the end effector and the ability to automate tasks.

The positional feedback can also be obtained using position trackers and external sensors. However, using such equipment would require additional space in the operating room. The most common types of position trackers are either optical or magnetic. Using an optical tracker requires a clear line of sight between the sensor and the reflectors, which is an issue with the number of people and instruments in the operating room. The magnetic trackers do not work well in an environment filled with ferrous metals, and the robots are made of metal which rules out their use. Moreover, using these sensors would increase the setup time. For these reasons, it may be desirable to have a system which does not add to the current equipment.

In the current robotic systems, the camera holder is operated by the surgeon to change the view. During a surgical task, if the surgeon wants to change the view, he has to switch between the tool control and camera control. This leads to some necessary down-time during the surgery. This can be avoided if the camera holder can adjust itself dynamically as required by the surgeon to give an optimal view of the surgical site. During surgery there are certain scenarios, like knot tying, in which the tools would go out of the camera view. In such cases the position of the camera can be autonomously adjusted so that the tools will always be in the view. In this type of control, the surgeon does not have to worry about switching the controls to change the view of the camera. The surgeon can move the tools wherever he/she wants to and the camera will automatically adjust itself so that the tools are centered. Such a system can reduce both effort and time required for the surgery.

In some systems, the position of the tools may be detected using the images from the laparoscopic camera. There are other image processing based systems to identify the position of the tools. The one problem with such systems is the reduced visibility of the tools during certain conditions of the surgery, where there is a lot of smoke and water vapor present. Reduced visibility can mislead image based systems and can lead to errors. This system may also encounter problems in detecting the tools due to specular reflection. Other systems may adjust the camera view based on the positions of the laparoscopic tools. This system relies on the images obtained from the camera view to determine the position of the tools. They also rely on special markings on the tools to enable tool detection. Other systems may control the camera based on the position of the tool, using electromagnetic position sensors to detect the position of the tool and the camera. Using sensors to detect the position of the tools adds to the already complex environment in the operating room. Also electromagnetic sensors do not work well near metals. On the other hand, with positional feedback from the robot, a system can be developed which can autonomously adjust the position of the camera so that the tools are always in the view.

In developing the systems described herein, the motion control hardware of the Zeus Surgical System was redesigned to perform MIS using the robot along with the positional feedback of the tool's end-effector and automation of surgical tasks. The another aim is to develop a control system for the AESOP Robot, which holds a laparoscopic camera, and autonomously adjust the position of the camera based on the position of the tools.

In the original Zeus Surgical system, the Zeus and AESOP Robots are controlled by the Zeus Master Controller, which houses all the control circuits for the robots. Because of its closed architecture, it is not possible to modify their system for our requirements. However, the cable connecting the master controller to the robots may be spliced to understand how it works and which wires control which parts of the robots.

The Zeus Robot is used to control the laparoscopic tools and is controlled by the surgeon using the master controller. The AESOP robot is used to control the laparoscopic camera and is controlled either by a remote or through voice commands. The mechanical structure of the Zeus and AESOP robots are similar, except for one extra joint on the Zeus robot. This makes it easy to develop the motion control systems and the kinematics for these robots.

Figure 5:
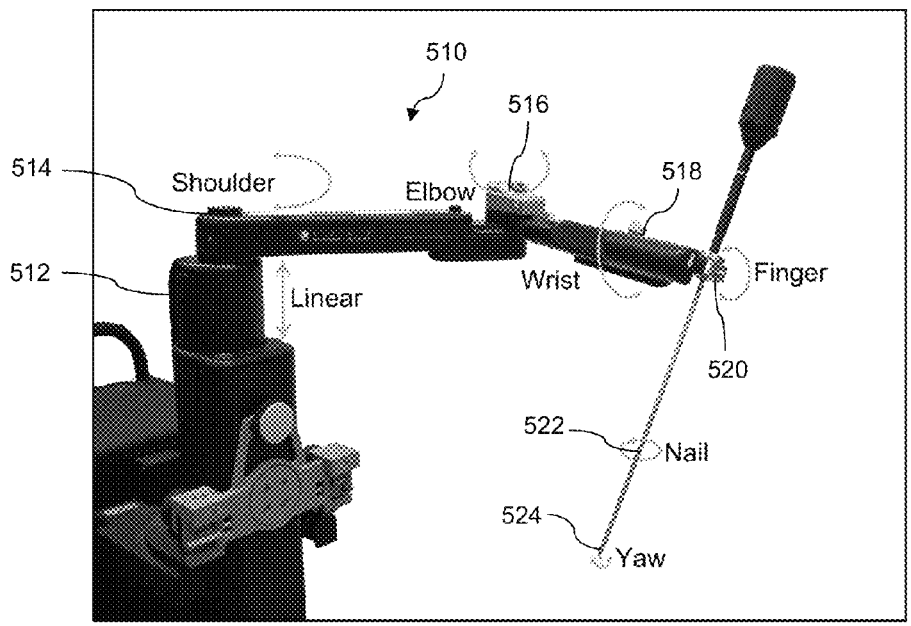
FIG. 5 is a picture of the Zeus robot with the names of each joint.

The Zeus robot 510 has seven joints in total. Out of the seven joints, five of them are active joints, e.g., their position can be controlled by the motors. The other two joints do not have motors and are called passive joints. All the joints have feedback mechanism. The active joints have encoders and potentiometers for feedback while the passive joints have only potentiometers for feedback. All the joints were given names for convenience of this description, they are 'Linear' 512, 'Shoulder' 514, 'Elbow' 516, 'Wrist' 518 'Finger' 520, 'Nail' 522 and 'Yaw' 524. Out of these, the 'Linear' 512, 'Shoulder' 514, 'Elbow' 516, 'Nail' 522 and 'Yaw' 524 are the active joints and the 'Wrist' 518 and 'Finger' 520 joints are passive. The 'Finger' and 'Yaw' joints were not used in testing the autonomous camera control project because they control only the orientation of the gripper and do not alter the position of the gripper and hence are not useful for tracking with the camera. FIG. 5 shows the Zeus robot and the names of each joint. The direction of motion of each joint is also denoted. All the joints except the 'Linear' joint 512 are rotary joints and the 'Linear' joint 512, as the name suggests, has linear motion.

Figure 6:
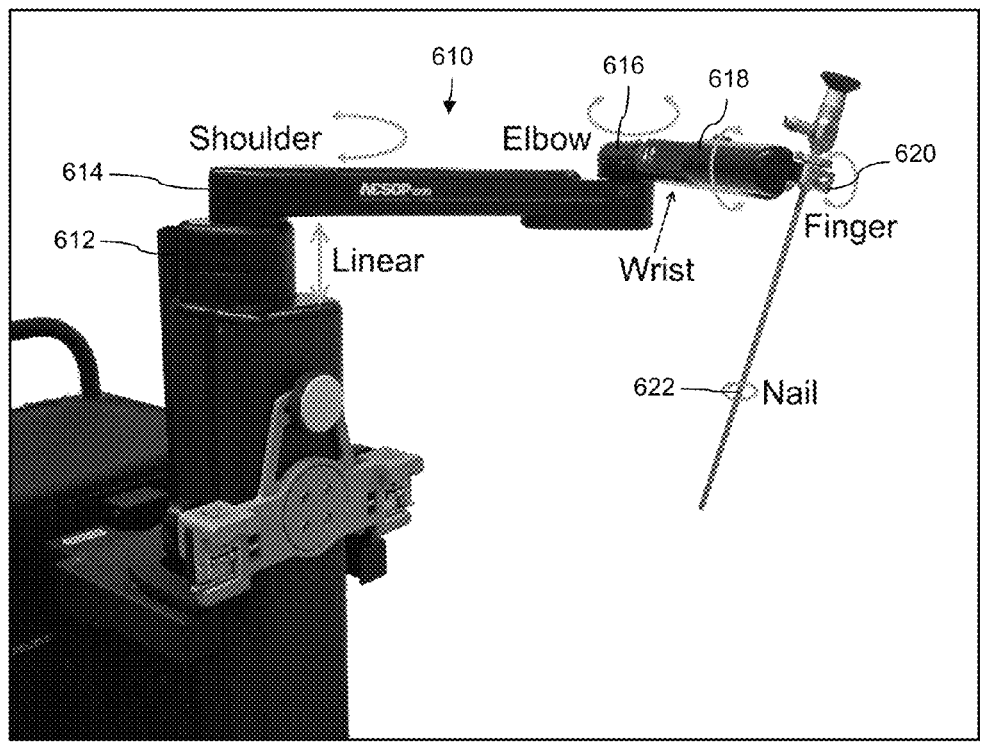
FIG. 6 is a picture the AESOP 1000 robot with the names of each joint.

The AESOP Robot 610 is very similar to the Zeus Robot 510. The only difference is that it does not have the 'Yaw' joint, which is in the Zeus Robot. The 'Linear' 612, 'Shoulder' 614, 'Elbow' 616 and 'Nail' 622 are the active joints and the 'Wrist' 618 and 'Finger' 620 joints are passive. The 'Nail' 622 joint in the AESOP robot controls the roll of the camera and was not used for testing this system. FIG. 6 shows the AESOP 1000 robot and the names of each joint. The directions that each joint of the robot moves is also denoted.

The AESOP robot also has encoders and potentiometers for the purpose of feedback.

The feedback from the joints can be used to calculate the joint angles. The encoders may be used in the active joints to calculate the angles and the potentiometers may be used in the passive joints. The encoder counts in the 'Linear' joints 612 provide the linear displacement of the joint and the encoder counts in the 'Shoulder' 614 and 'Elbow' 616 give the angular displacement of the joint with respect to the X-axis of the robot. The potentiometer readings provide the angular displacement of the passive joints with respect to their previous joints.

The 'Shoulder' 614 and the 'Elbow' 616 joints in both Zeus and AESOP robots are linked to each other. When the 'Shoulder' joint 614 is moved in the clock wise direction, the 'Elbow' joint 616 moves in the counterclockwise direction and if the 'Shoulder' joint 614 is moved in the counterclockwise direction, the 'Elbow' joint 616 moves in the clockwise direction. However, when the 'Elbow' joint 616 is moved, it does not affect the 'Shoulder' joint 614. This causes problems when measuring the joint angles.

The link between the 'Shoulder' and 'Elbow' joint 612, 614 means that when the 'Shoulder' 612 is moved, the encoder value at the 'Elbow' joint 614 also changes and hence results in a change in the angle even when the 'Elbow' joint 614 is not moved. In order to avoid this problem, the angle of the 'Shoulder' joint 612 is subtracted from the value of the 'Elbow' joint 614 to obtain the angle of the 'Elbow' joint 614 with respect to the 'Shoulder' joint 612.

Figure 7:
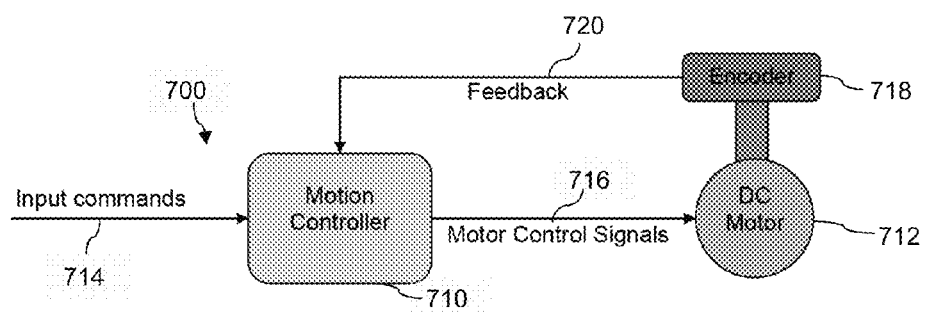
FIG. 7 is a block diagram of a motion controller setup.

Motion Controllers are typically electronic circuits used to control robotic arms or manipulators using motors and drives. They usually provide position or velocity control of each motor. They are closed loop control systems which control the motors based on the feedback from the motor shaft. The feedback can be either in the form of a quadrature encoder or a potentiometer. FIG. 7 shows the basic block diagram of a motion controller setup, where the controller controls a D.C. Motor based on the feedback from encoder connected to the shaft of the motor.

The motion controller used to control Zeus and AESOP robots is the Galil DMC-21×3 Controller. FIG. 7 is a block diagram of the setup of a motion controller system 700. Figure shows a motion controller 710 used to control a D.C. Motor 712 at each joint of the robot using encoders as feedback. The input command 714 can be either a target position or target speed and the controller generates motor control signals 716 to manipulate controls the position or speed of the motor 712 based on the input 714. The motion controller 710 may use encoders 718 connected to the motor 712 to generate a feedback signal 720 to the motion controller 710.

The Galil Motion Controller DMC21×3 has the ability to control D.C. motors with encoder feedback and can also read the potentiometer values. It provides two options for communication, through RS-232 communication or Ethernet. DMC Smart Terminal, software provided by Galil, is used to establish communication with the motion controller and to control the robots. The communication libraries are also provided which allows building software in C++ to communicate with the motion controller and control the robot. Two motion controllers were used for the project, one for each robot. The DMC2183 controller (can control up to 8 motors) is used to control the Zeus robot and the DMC2143 controller (can control up to 4 motors) is used to control the AESOP robot.

The motion controller contains an amplifier board which provides the connectors to connect to the motors and the encoders. This board amplifies the control signals before sending them to the motors. Each pair of connectors is named as 'X', 'Y', 'Z' and 'W'. The motion controller also has a separate board to read analog signals. This board is used to read the potentiometer values from the passive joints. The controller provides a wide range of commands to control the motors and get feedback from the encoders. The ones used commonly for testing this implementation are listed below.

Galil Motion Controller Commands

1. Position Relative (PR)

This command is used to set the incremental distance and direction of the next move in encoder counts. The move is relative to the current position. Ex:

PRX=10000, where X indicates the joint to be moved. This command tells the controller to move the X joint 10000 encoder counts in the positive direction from the current position.

2. Position Absolute (PA)

This command is similar to the PR command, but the move is referenced to absolute zero. Ex: PAY=5000. This command tells the controller to move the Y joint to the 50 oath encoder count relative to the absolute zero.

3. Begin Movement (BG)

This command tells the controller to begin the motion of the specified joint. This can be used to synchronize the movements of multiple joint. Ex: BGXY. This command starts moving the X and Y joints to the target specified by either the PR or PA commands.

4. Tell Position (TP)

This command returns the current value of the encoder of the joint specified. Ex:

$T_{PZ}$. When the controller receives this command, it returns the encoder value of the Z axis.

5. Speed (SP)

This command is used to set the speed at which the joint moves. The units are encoder counts per second. Ex: SPX=5000. This command sets the speed of X joint to 5000 encoder counts per second and any motion is executed at that speed.

6. Acceleration (AC)

This command sets the linear acceleration rate for the specified joints. The units are in encoder counts per second squared. Ex: ACX=20000. This command sets the linear acceleration for the X joint to 20000.

7. Deceleration (DC)

This command sets the linear deceleration rate for the specified joints. The units are in encoder counts per second squared. Ex: DCX=20000. This command sets the linear deceleration for the X joint to 20000.

8. Stop (ST)

This command is used to stop the motion on the specified joints. It brings the joint to a decelerated stop. Ex: STZ. This command stops the motion of the Z joint.

9. Abort (AB)

This command brings the specified joint to an abrupt stop without any controller deceleration. Ex: ABX. This command aborts any motion on the X axis.

10. Jog (JG)

This command sets the specified joint to jog mode and specifies the jog speed for that joint. When this command is sent, the joint keeps moving in the specified direction at the specified jog speed until an abort command is sent. Ex:

JGX=5000. This command sets the jog speed to 5000 encoder counts per second and begins the motion when BG command is received.

11. Tell Torque (TT)

This command reports the amount of torque on the specified joint. Its value is between −9.998 to 9.998 volts. Ex: TTY. This command returns the torque on the Y joint.

12. Define Position (OP)

This command sets the current position of the motor to a user specified value. The units are encoder counts. Ex: DPX=O. This command sets the encoder value of the X joint to zero.

13. Tell Error (TE)

This command returns the current position error of the motors. The units are encoder counts. Ex: TEZ. This command returns the current error on the Z axis.

For a complete list of the commands and details about their usage, please refer to the Command Reference Manual for the DMC21×3 Motion Controller.

The Zeus and AESOP robots fall under the category of manipulator arms, which are basically a series of joints attached to one another. The 'Linear' joint is connected to the base of the robot at one end and to the 'Shoulder' joint at the other end. Similarly, one end of the 'Elbow' is connected to the 'Shoulder' and the other end is connected to the 'Wrist'. This way the whole robot comprises of links and joints connected to one another to form the kinematic model of the whole robot. The calculations involved in controlling each joint to position the end-effector at the target position and orientation is called kinematics of the robot. This involves two types of calculations. They are:

1. Forward Kinematics: The calculations in which the angle and position of each joint with respect to its previous joint is known and they are used to calculate the position and orientation of the end-effector is known as forward kinematics.

2. Inverse Kinematics: The calculations in which the position and orientation of the end-effector is known and is used to calculate the angle and position at which each joint should be for the end-effector to reach the required position and orientation is known as inverse kinematics.

To control the robot and to calculate the kinematics of the robot, it is necessary for us to know the angle of each joint, with respect to the previous joint. These robots have five joints, out of which three are active and two are passive (Zeus has two additional active joints and AESOP has one active joint but these joints were not used for testing this project). The active joints, which can be controlled by motors, comprise optical encoders and potentiometers to provide positional feedback. The passive joints are free moving joints and their position depends on the positions of the active joints and the trocar point through which the tool is placed. The passive joints have only potentiometers for positional feedback.

In order to get the conversion between the encoder counts at the joints of the robot and the angles, the total span on each joint and the total range of the corresponding encoder can be measured. Using this data, the number of encoder counts required to move a joint by one degree can be determined. The encoder count of each joint is obtained from the Galil Motion Controller. The position of each joint, in mm/rad, may be obtained from a Polaris Tracking System. Polaris is an optical tracking instrument which is used to get the position of a point in 3D space. It uses infra-red light and cameras to track specific tools, with infrared reflectors, in 3D space.

Figure 8:
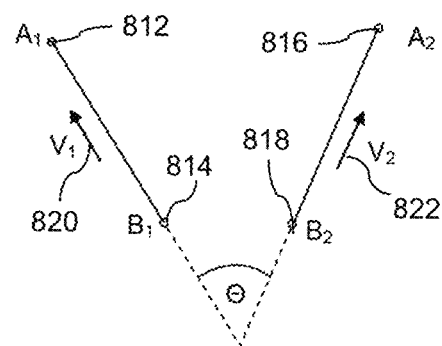
FIG. 8 is a vector diagram of the tracked points on the joint.

The tip of the tracking tool is placed at two different points of a joint, with the joints at different positions. The positions of the tip are recorded and then used to calculate the angle between each orientation of the joint. Two points on the joint were chosen and the tracking tool was placed on these points to record the position of the two points, while the joint was moved along its range of motion. While recording the position of the tracking tool tip, the encoder count of the joint is also recorded. FIG. 8 shows a vector diagram of the tracked points on the joint. A1 and B1 are the points 812, 814 on the joint at position 1 and $A_2$ and $B_2$ are the points 816, 818 on the joint at position 2. $V_1$ is the vector 820 from $B_1$ to $A_1$ and $V_2$ is the vector 822 from $B_2$ to $A_2$. θ is the angle between $V_1$ and $V_2$.

The angle, θ is calculated using the following formula.

$$\theta = \cos^{-1} \frac{\vec{V_1} \cdot \vec{V_2}}{|V_1| * |V_2|} \quad \text{Equation 1}$$

The measurements were taken all along the range of the motion of the joints and the average encoder counts per radian were calculated. This was done for both the Zeus and AESOP robots. The calculated conversion factors are:

Conversion factors for Zeus Robot:

TABLE 1

| Joint Name | Encoder Counts |
| --- | --- |
| Linear | 173.8779707/mm |
| Shoulder | −21113.92907/radian |
| Elbow | −21425.51029/radian |

Conversion factors for AESOP Robot:

TABLE 2

| Joint Name | Encoder Counts |
| --- | --- |
| Linear | −792.6891211/mm |
| Shoulder | 131582.8693/radian |
| Elbow | −114998.1311/radian |

Since there was no way to control the position of the passive joints and the inability to use conventional methods like protractors and scales, a camera was used to take pictures and measure the angles. The camera was placed at a level, which is parallel to the robot's arm. Then, pictures of the joint at different positions were taken and the corresponding potentiometer readings were noted. Then a line on the joint and the base are taken and the angle between the lines is measured.

Figure 9:
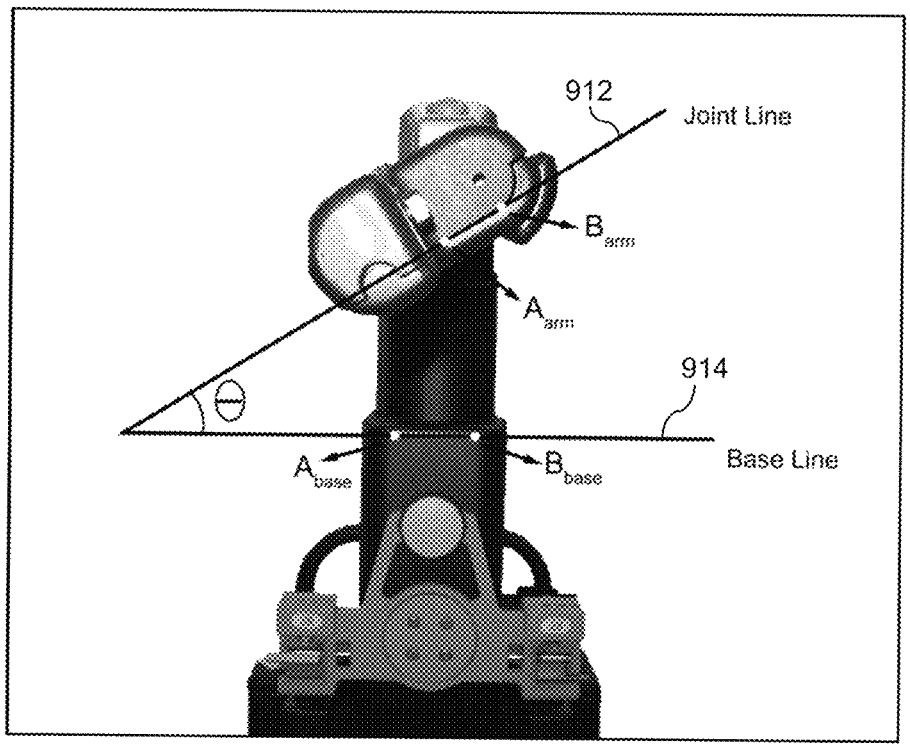
FIG. 9 is a picture illustrating the pixel positions of the points $A_{arm}$, $B_{arm}$, $A_{base}$ and $B_{base}$.

As shown in FIG. 9, the pixel positions of the points $A_{arm}$, $B_{arm}$, $A_{base}$ and $B_{base}$ were noted down. These pixel positions were taken as the co-ordinate points in a plane parallel to the face of the camera. The slopes of the 'Joint Line' ($AB_{arm}$) 912 and the 'Base Line' ($AB_{base}$) 914 may be calculated. Further, the angle between the lines is calculated using these slopes.

Figure 10:
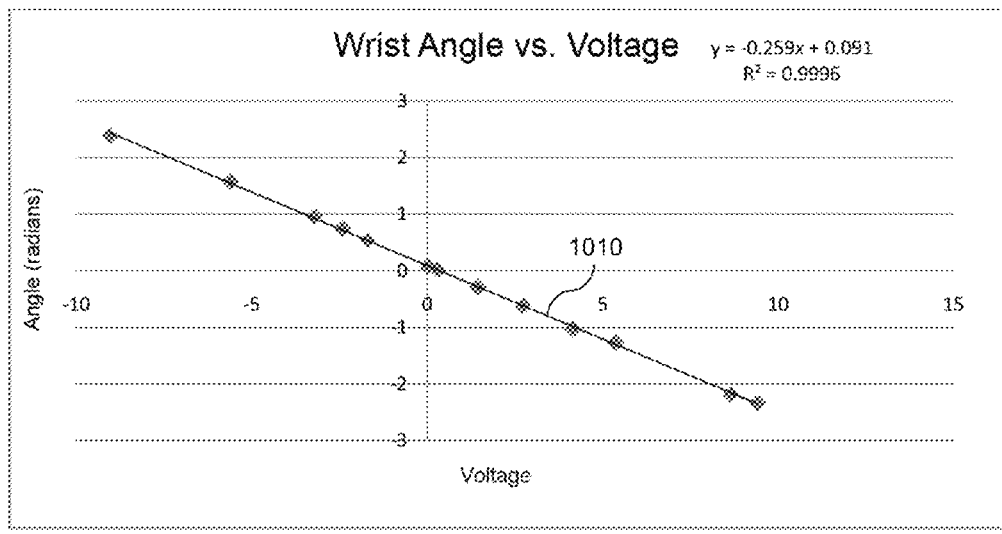
FIG. 10 is a graph illustrating the plot between the angle of the wrist and the voltage for the Zeus robot.

Following the same procedure, the angles between the arm and the base may be calculated and the corresponding potentiometer values may be taken. A graph may be plotted between the angle and the voltage. FIG. 10 shows the plot

1010 between the angle of the wrist and the voltage for the Zeus robot. A linear relation was obtained between the voltage and angle. The calculated relation for the wrist joint of the Zeus Robot is:

$$\text{Angle} = -0.259 * \text{Voltage} + 0.091 \quad \text{Equation 2}$$

Figure 11:
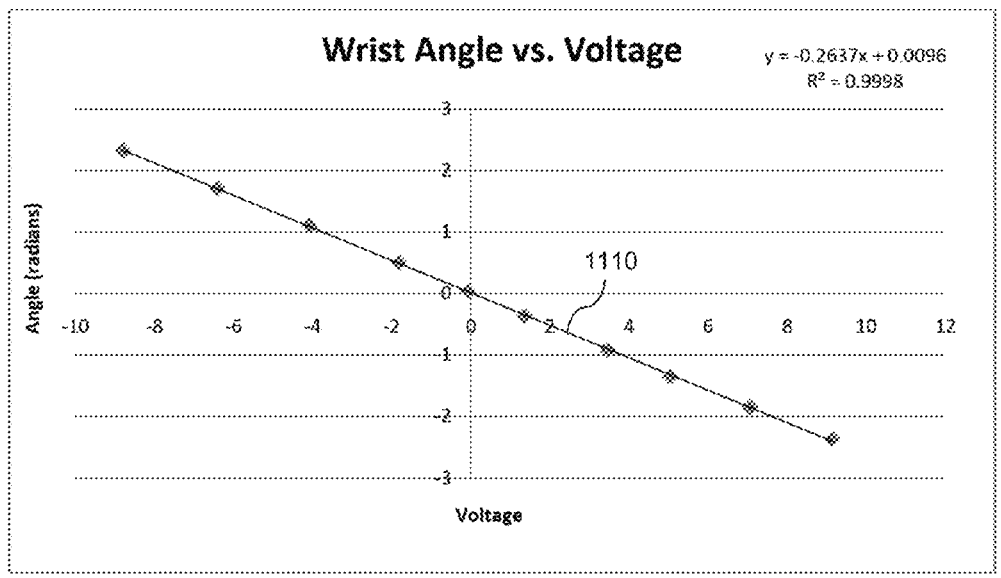
FIG. 11 is a graph illustrating the plot between the angle of the wrist and the voltage for the AESOP robot.

The same procedure may be followed to obtain the relation between the voltages and joint angles for the AESOP Robot. FIG. 11 shows the plot 1110 between the angle of the wrist and the voltage for the AESOP robot. The calculated relation for the wrist joint of the AESOP Robot is:

$$\text{Angle} = -0.2637 * \text{Voltage} + 0.0096 \quad \text{Equation 3}$$

Figure 12:
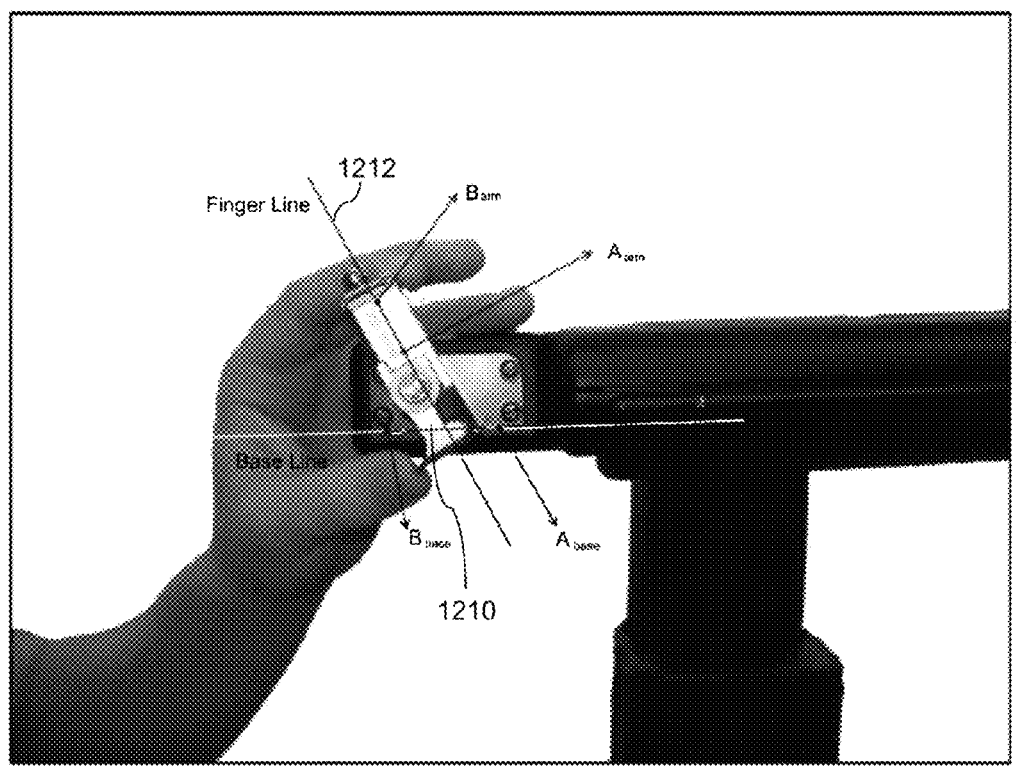
FIG. 12 is a picture illustrating the points taken on the finger joint for the calculations.

In a similar way, the joint angles for the finger may be measured and plotted against the corresponding voltages. FIG. 12 shows the points taken on the finger joint for the calculations, including two points on the base $A_{base}$ and $B_{base}$ to form the base line 1210 and two points on the figure $A_{arm}$ and $B_{arm}$ to form the arm line 1212.

Figure 13:
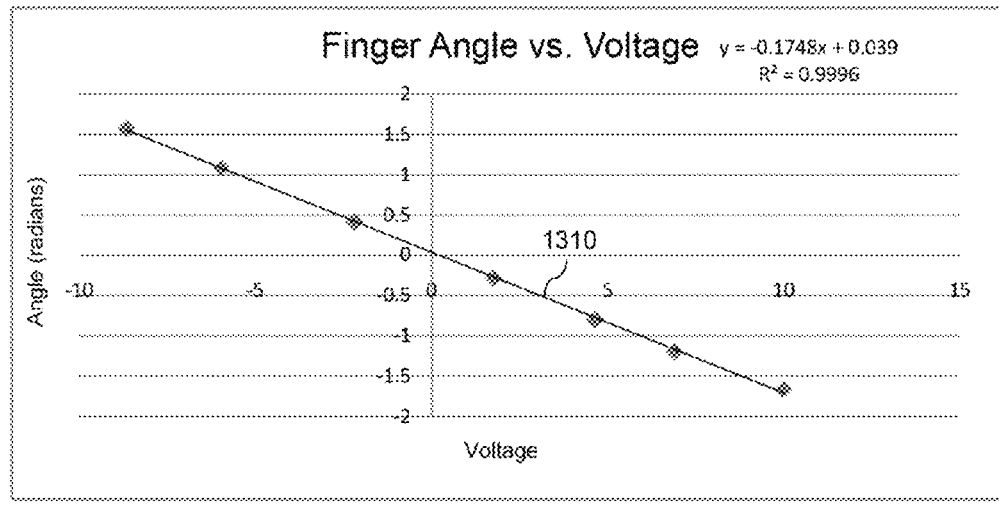
FIG. 13 is a graph illustrating the plot between the angle of the finger and voltage for the Zeus robot.

FIG. 13 shows the plot 1310 between the angle of the finger and voltage for the Zeus robot. The obtained relation for the Zeus Robot was:

$$\text{Angle} = -0.1748 * \text{Voltage} + 0.039 \quad \text{Equation 4}$$

Figure 14:
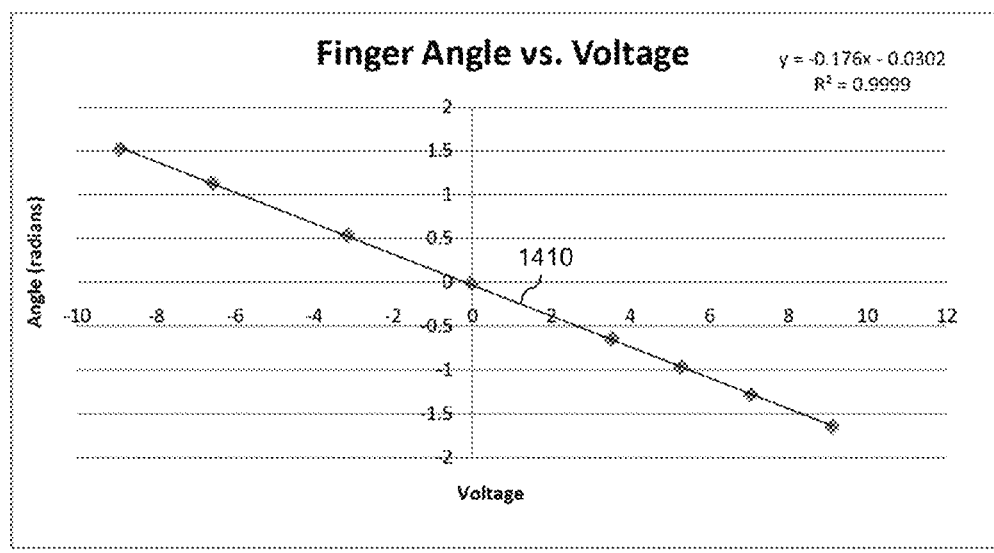
FIG. 14 is a graph illustrating the plot between the angle of the finger and voltage for the AESOP robot.

FIG. 14 shows the plot 1410 between the angle of the finger and voltage for the AESOP robot. The obtained relation for the finger joint of the AESOP Robot is:

$$\text{Angle} = -0.176 * \text{Voltage} - 0.0302 \quad \text{Equation 5}$$

In all multi-link robots, each link is connected to another link and the relation between them is given by the homogeneous transformation matrix between each pair of the links connected at a joint. A commonly used convention to represent the transformation matrices is the Oenavit and Hartenberg Convention [19]. In this convention, each homogeneous transformation is represented by four parameters called O-H Parameters. O-H Parameters are essential to calculate the kinematics of any robot. The O-H Parameters for the Zeus robot are obtained from Martinsen [20]. Table 3 shows the O-H Parameters of the Zeus robot.

TABLE 3

D-H Parameters of the Zeus Robot.

| Link | a | α | d | θ | Joint Type | Hardware Joint |
|---|---|---|---|---|---|---|
| 1 | 0 | 0 | 0 | 0 | Translational | Linear |
| 2 | 384.44 | 0 | 0 | 0 | Rotational | Shoulder |
| 3 | 52.71 | pi/2 | 0 | 0 | Rotational | Elbow |
| 4 | 0 | Pi/2 | 0 | Pi/2 | Non-Moveable | Dummy |
| 5 | 0 | Pi/2 | 250.7 | Pi | Rotational | Wrist |
| 6 | 17.2 | −pi/2 | 0 | Pi/2 | Rotational | Finger |
| 7 | 0 | Pi | 0 | 0 | Rotational | Nail |

The D-H Parameters for the AESOP robot may be obtained by measuring the distance between each joint using Vernier Calipers. Table 4 shows the O-H Parameters of the AESOP robot.

These D-H Parameters may be used to calculate and generate the homogeneous transformation matrices for each joint and may be used to calculate the forward kinematics and inverse kinematics of the robot.

TABLE 4

Table 4: D-H Parameters of the AESOP 1000 Robot.

| Link | a | α | d | θ | Joint Type | Hardware Joint |
|---|---|---|---|---|---|---|
| 1 | 0 | 0 | 0 | 0 | Translational | Linear |
| 2 | 384.44 | 0 | 0 | 0 | Rotational | Shoulder |
| 3 | 52.71 | pi/2 | 0 | 0 | Rotational | Elbow |
| 4 | 0 | pi/2 | 0 | pi/2 | Non-Moveable | Dummy |
| 5 | 0 | pi/2 | 250.7 | pi | Rotational | Wrist |
| 6 | 17.2 | −pi/2 | 0 | pi/2 | Rotational | Finger |
| 7 | 0 | pi | 0 | −pi/2 | Rotational | Nail |

Figure 15:
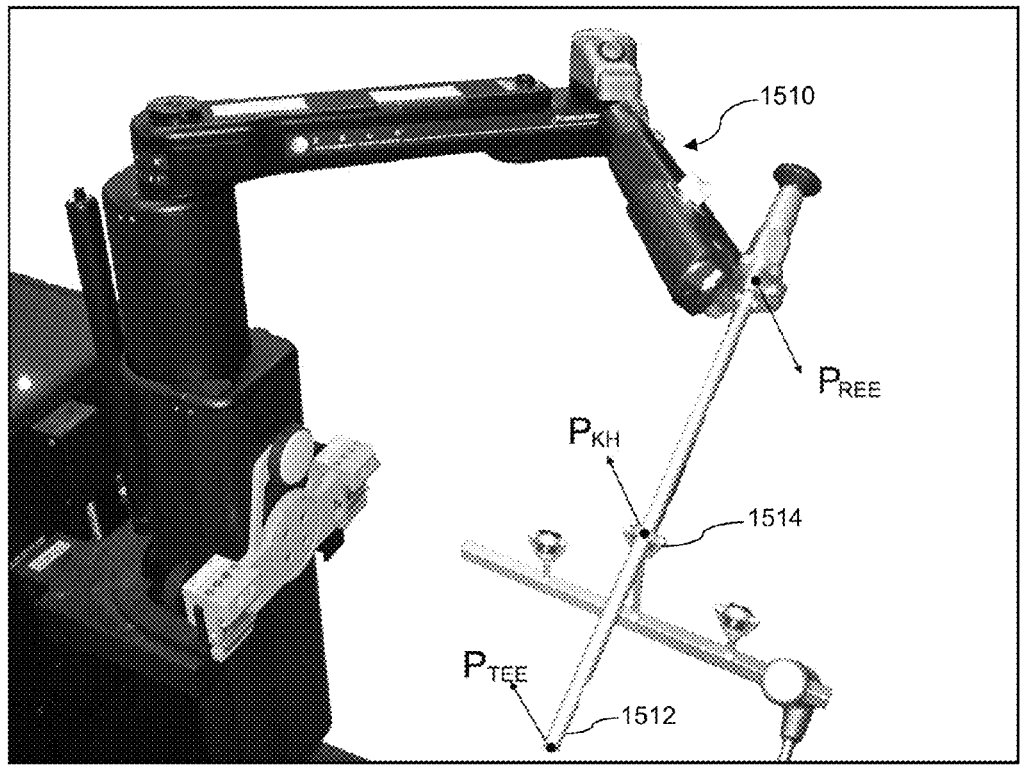
FIG. 15 is an illustration of the Zeus robot holding the tool and the trocar point.

In addition, a direct solution for the inverse kinematics of the robots may be implemented. As discussed earlier, the robots have two passive joints, which cannot be controlled by motors and whose position depends on the position of the trocar through which the tool is inserted. FIG. 15 shows the Zeus robot 1510 holding the tool 1512 and the trocar point key hole 1514. $P_{TEE}$ is the position of the tool's end-effector; $P_{KH}$ is the position of the key hole, and $P_{REE}$ is the position of the robot's end-effector at which the tool is held.

The position $P_{KH}$ is registered initially with respect to the base of the Zeus robot. If $P_{TEE}$ is the desired position of the tool, then, since the tool is rigid, there can only be one $P_{REE}$. Therefore the position $P_{REE}$ is calculated by projecting $P_{TEE}$ through $P_{KH}$.

However, the point $P_{REE}$ is located in the center of the 'Nail' joint, which is a connected to a passive joint (Finger) and its position cannot be controlled. Hence, this point can be transformed to another point on the robot which can be controlled. It has been observed that the center of the joint between 'Finger' and 'Wrist' (say P) always lies along the axis of the 'Elbow' joint, which is an active joint and can be controlled. So, for the purpose of the inverse kinematics calculations, the axis along the 'Elbow' joint and the point 'P' can be considered to be one single joint and the point '$P_{REE}$' is transformed to point 'P'.

It should also be noted that the only movable joint between the 'Finger' and 'Nail' is the joint which controls the roll of the end-effector and that it is not being for this project. Hence, the transformation between the point 'P' and '$P_{REE}$' may be fixed no matter what the position and orientation of the other joints are. This allows the transformation to be calculated between these two points during the registration stage and used it for the calculations.

The transformation between 'P' and 'PREE' is calculated while the key-hole (PKH) is being registered. Now the transformation matrix from '$P_{REE}$' to 'P' would be the inverse of the transformation between 'P' and '$P_{REE}$'. Whenever, the inverse kinematics solution has to be calculated, the point '$P_{TEE}$' may be transferred to '$P_{REE}$' and then transferred to point 'P'.

Once the point 'P' is known, the robot effectively operates as a 3 joint robot with the 'Linear', 'Shoulder' and 'Elbow' joints. Although the 'Elbow' joint now constitutes the 'Elbow' and 'Wrist' joints with point 'P' as the end of the joint. The point 'P' is a point in the 3D space with respect to the base of the robot with 'X', and 'Y' and 'Z' as the three coordinates of the point. The value of 'Z' holds a linear relation to the height of the linear joint and hence can be calculated using the formula:

$$\text{Length of Linear Joint} = Z - O_{LS} - O_{SE} \quad \text{Equation 6}$$

Where, $O_{LS}$=Offset between Linear Joint and Shoulder joint.

$O_{SE}$=Offset between Shoulder Joint and Elbow joint.

Once the length of the linear joint to reach the 'Z' co-ordinate is calculated, the joint angles for the 'Shoulder' and 'Elbow' joints should be calculated to reach the 'X' and 'Y' co-ordinates.

Figure 16:
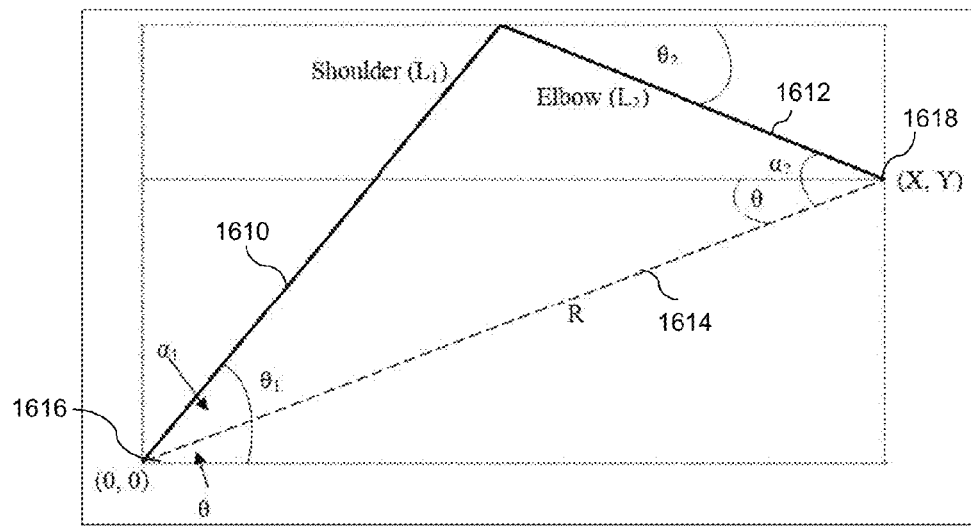
FIG. 16 is a diagram for the inverse kinematics calculations for the 'Shoulder' and 'Elbow' joints.

FIG. 16 shows the diagram for the inverse kinematics calculations for the 'Shoulder' and 'Elbow' joints. In the diagram, '$L_1$' and '$L_2$' are the length 1610 of the 'Shoulder' joint and the length 1612 of the 'Elbow' joint respectively. 'R' is the distance 614 between the origin 1616, 'O' and the point 'P' 1618, which is shown in FIG. 16 with its 'X' and 'Y' co-ordinates. '$\theta_1$' and '$\theta_2$' are the angles of the 'Shoulder' and 'Elbow' joints with respect to the 'X' axis. '$\theta$' is the angle between the line joining 'O' and 'P' with respect to the 'X' axis. '$\alpha_1$' is the angle between the 'Shoulder' and "OP" and '$\alpha_2$' is the angle between 'Elbow' and 'OP'.

Now, $$R = \sqrt{X^2 + Y^2} \quad \text{Equation 7}$$

$$\theta = \tan^{-1}\frac{Y}{X} \quad \text{Equation 8}$$

$$\alpha_1 = \pm\cos^{-1}\left[\frac{R^2 + L_1^2 - L_2^2}{2*R*L_1}\right] \quad \text{Equation 9}$$

$$\alpha_2 = \pm\cos^{-1}\left[\frac{R^2 + L_2^2 - L_1^2}{2*R*L_2}\right] \quad \text{Equation 10}$$

$$\theta_1 = \alpha_1 + \theta \quad \text{Equation 11}$$

$$\theta_2 = \alpha_2 - \theta \quad \text{Equation 12}$$

Using the above calculations, the values of $\theta_1$ and $\theta_2$ may be calculated. Hence the joint angles of the 'Linear', 'Shoulder' and 'Elbow' joints may be calculated using the above equations. The joint angles may be converted into encoder counts and then commands may be sent to the motion controller to move the joints to the corresponding positions. This way, whenever the tool has to be placed at position 'PTEE', the inverse kinematics algorithm performs the above state calculations and moves the tool to the required position.

As discussed earlier, the motion control system for the Zeus and AESOP robots and the basic control algorithms can be developed. The next step in the project is to allow the Zeus robot to perform tele-operation. This chapter explains how the tele-operation of the Zeus robot is done using the motion control system described herein.

In the original Zeus system the surgeon or the operator sits at the Master Console and operates the tools on the robots using the two controllers. All the motions of the two controllers are transformed into the motion of the robot end-effectors. The Master Console also has the 'Clutch' which helps the user to reset the positions of the controllers. It also has features like 'Motion Scaling' and 'Tremor Filtration'.

Each controller at the Master Console has multiple joints named 'Shoulder', 'Slider', 'Pitch', 'Roll', 'Yaw' and 'Gripper'. Each joint has positional feedback mechanisms in the form of either encoders or potentiometers. The electronics and the control hardware of the Zeus system may read the values of these encoders and potentiometers from each joint and then may translate these values into control signals for the motors on the joints.

In order to track the motion of the two controllers at the Master Console, Sachin Motion Tracking hardware may be connected to the Zeus controllers electronic hardware to track the values the encoders and potentiometers of each joint. The motion tracking hardware may also track the value of the clutch. This hardware may have a serial port through which it sends out these values to any computer. In order to be able to read these values and track the position and orientation of the controller, a software library may be developed. These libraries may be used in the control software to track the position and orientation of the controllers.

Zeus Master Controller Library

This library provides routines to do the following essential functions:

1. Establish communication with the motion tracking hardware.
2. Read the encoder and potentiometer values.
3. Convert them to joint angles.
4. Calculate position and orientation of the controllers.
5. Track the state of the clutch.
6. Track the state of the gripper.
7. Track the state of the buttons.

Using this software library, the position and orientation of the master controllers may be obtained and used in the control software to perform the tele-operation of the Zeus robot.

It has been observed in the original Zeus system that during tele-operation, the motion of each joint in the Zeus robot is linked to the motion of one joint in the master controller. The following table lists the link between each joint of the robot and the controller.

TABLE 5

| Joint on the Zeus Robot | Corresponding joint on the controller |
| --- | --- |
| Linear | Slider |
| Shoulder | Shoulder |
| Elbow | Linear |
| Nail | Roll |
| Yaw | Yaw |
| Gripper | Gripper |

Since the system may be configured so that the orientation of the tool does not affect the tracking of the camera, the 'Nail' and 'Yaw' joints of the Zeus robot are not controlled.

Figure 17:
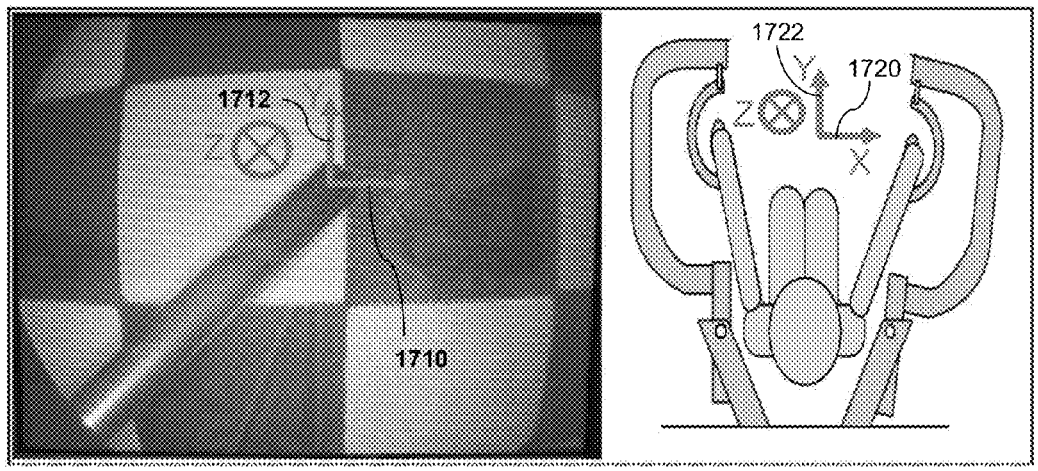
FIG. 17a is a picture illustrating the co-ordinate system in the camera view on the left side.
FIG. 17b is a diagram illustrating the co-ordinate system for the master controller.

FIG. 17a shows the co-ordinate system in the camera view on the left side. The horizontal axis 1710 in the camera view is the X-axis, the vertical axis 1712 in the camera view is the Y-axis and the Z-axis is into the screen. The same notation may be followed at the master controller, which is shown in FIG. 17b. This way when the user moves the master controller in the positive X direction 1720, the tool also moves in the positive X direction. Similarly, when the user moves the master controller in the positive Y direction 1722, the tool also moves in the positive Y direction. However, it may be assumed that the camera does not roll. If the camera rolls, the axes in the camera view change and they are no longer related to the axes at the master controller. This issue will be discussed further below.

Figure 18:
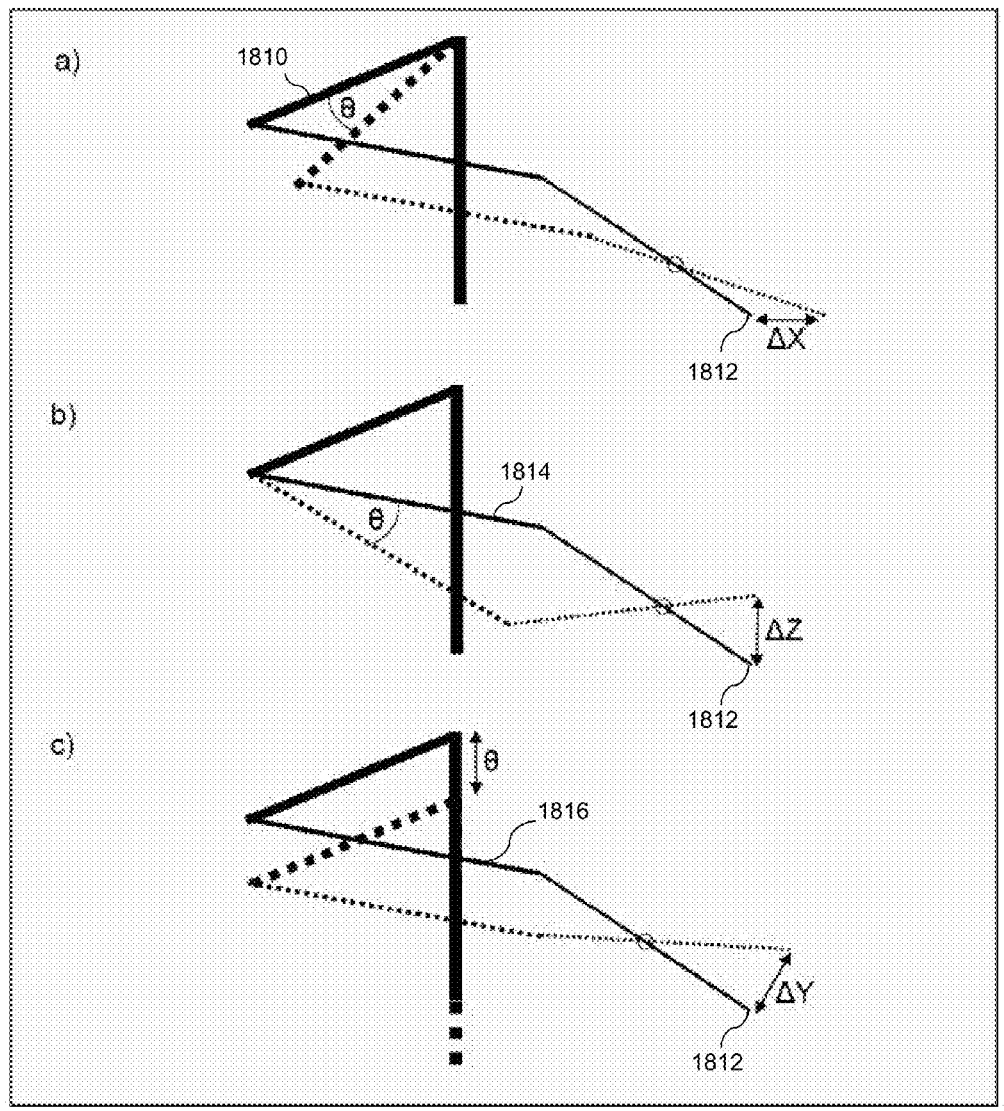
FIGS. 18a-c are illustrations illustrating how the motion of each joint affects the position of the end-effector.

FIGS. 18a-c shows how the motion of each joint affects the position of the end-effector. FIG. 18a shows that the 'Shoulder' joint 1810 moves the end-effector 1812 in the X direction, the 'Elbow' joint 1814 moves the end-effector in the Z direction and the 'Linear' joint 1816 moves the end-effector along the Y axis. This relation is used to perform the tele-operation of the Zeus robot. When the master controller is moved the change in the position along each axis is measured and that difference is multiplied by a constant factor to convert it into the corresponding encoder counts for each joint. The motion commands are sent to the robot. As a result, the robot moves according to the motion of the master controllers and hence performs the tele-operation.

The Jog (JG) command may be used to control the robot as it allows for continuous motion of the joints. The jog speed may be proportional to the difference in the position of the master controller. This way, if the master controller is moved at high speeds, the jog speed increases and results in the faster motion of the end-effector. If the master controller is moved at low speeds, the jog speed decreases and results in the slower motion of the end-effector.

Figure 19:
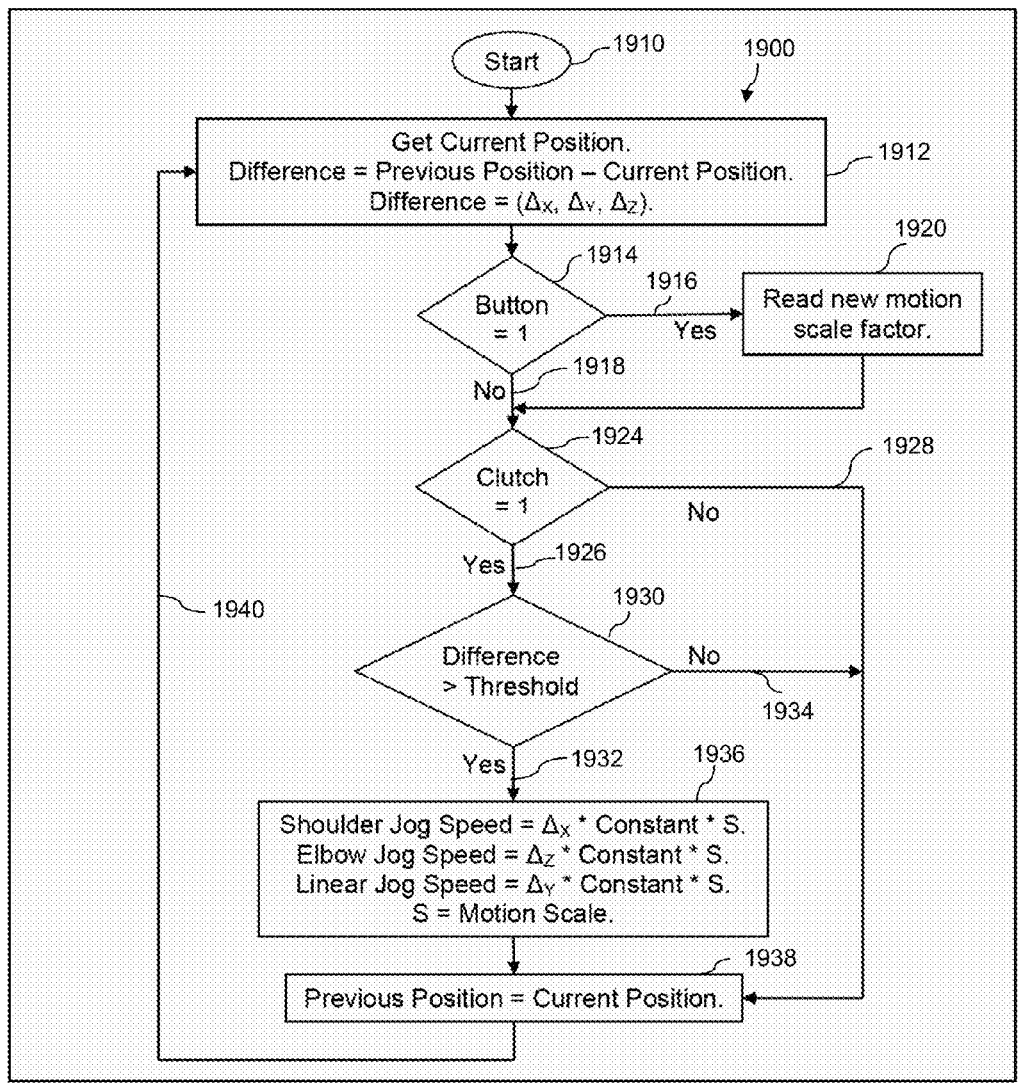
FIG. 19 is a flow chart describing a method for tele-operation of a robot.

FIG. 19 shows a flow chart describing a method 1900, such as a program for tele-operation of a Zeus robot. The method starts in step 1910. In step 1912, the program retrieves the current position of the master controller. This step may also include getting the state of the buttons on the master controller and the clutch. The current position may be then compared to the previous position to calculate the difference of position in each axis. In step 1914, the state of the button assigned for motion scale is checked. If the button is pressed, the method follows line 1916, the user may be asked to input the new motion scaling factor in step 1920. The default value for the motion scale may be five and the user can input any value between 1 and 10. If the button is not pressed, the method follows line 1918. In step 1924, the state of the clutch may be checked. In step 1924, if the clutch is pressed, the method follows line 1926 and the jog speeds for each joint may be calculated and sent to the motion controller. For example, in step 1936, if the clutch is not pressed, the method follows line 1928 and system skips the calculation of the jog speeds and sends an abort command to the robot to stop the previous jog motion (Jog command moves the robot continuously at the specified speed until an abort command is sent). In either scenario, the current position is updated in step 1938 and the method follows 1940 to step 1912 when the method continues.

This way, the end-effector follows the motion of the controller. The motion scale factor allows the system to adjust the motion scale such that large motions (in cm) at the master controller can be translated to minute motions at the end-effector (in mm).

Another function in the program may be tremor filtration. This is done by comparing the difference between the present and previous positions of the controller with a defined threshold as denoted by step 1930. If the difference is greater than the threshold, the method follows line 1932 and the motion commands are sent. If the difference is less than the threshold, the method follows line 1934, the motion commands are not sent. This way the tremors at the controller (which is usually a minute motion) do not have any effect on the motion of the robot and as a result, the tremors are filtered.

The optimum values for the constants like the threshold and the constants used to convert the difference to jog speeds may be obtained by trial and error. Thus this program restores the tele-operation of the Zeus robot, along with the motion scaling, tremor filtration and clutch.

Autonomous camera control involves tracking the position of the tool and the camera and then calculating the position of the tool with respect to the camera. Once the position of the tool with respect to the camera is found, the program can calculate the appropriate position for the camera so that the tool is always in the view.

Two control strategies may be developed for the camera placement. They are:

1. Adjust the zoom level of the camera based on the tool position.
2. Follow the tool so that the tool is in the center of the view.

Figure 20:
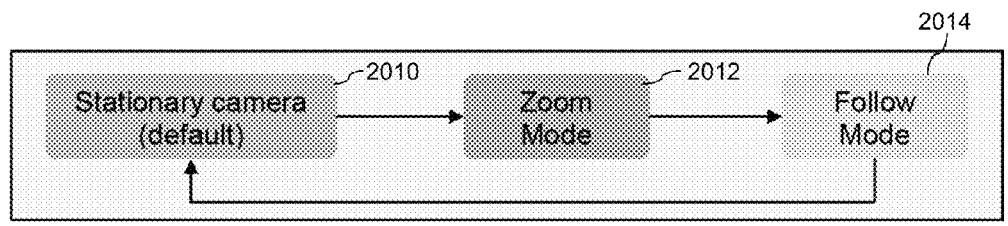
FIG. 20 is a flow chart illustrating a method for selecting the control mode.

The user can control the mode by pressing a button on the master controller. This is illustrated in FIG. 20. By default, the camera does not move with respect to the tool, as denoted by block 2010. If the button is pressed once, the control mode may switch to Zoom Mode as denoted by block 2012. If the button is pressed again, the control mode may switch to Follow Mode as denoted by block 2014. If the button is pressed again, the camera may stay stationary and go into the default mode 2010.

Figure 21:
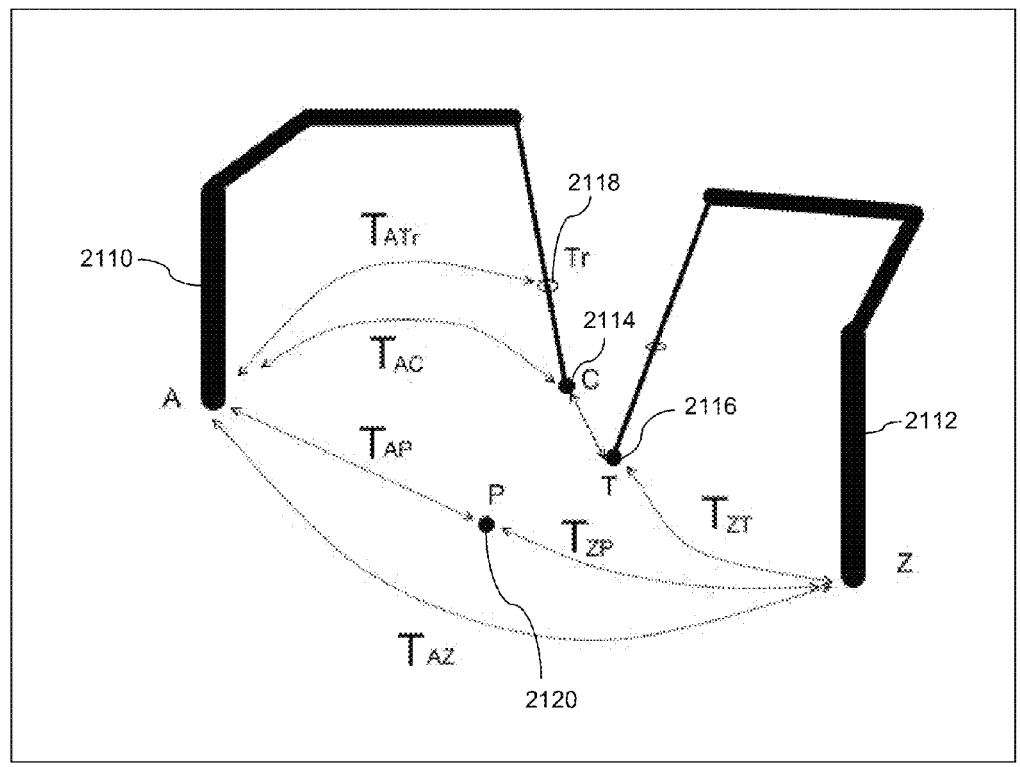
FIG. 21 is a diagram illustrating all the transformations between the Zeus and AESOP Robots.

In FIG. 21, 'A' and 'Z' are the bases of AESOP Robot 2110 and Zeus Robot 2112, respectively. 'C' is the camera 2114 and 'T' is the tool 2116. 'Tr' is the trocar 2118, and 'P' is a registration point 2120. '$T_{ZT}$' is the transformation between 'Z' and 'T'. '$T_{AC}$' is the transformation between 'A' and 'C'. '$T_{AP}$' is the transformation between 'A' and 'P'. '$T_{ZP}$' is the transformation between 'Z' and 'P'. '$T_{ATr}$' is the transformation between the 'A' and $T_r$. '$T_{AZ}$' is the transformation between 'A' and 'Z'.

'$T_{AC}$' and '$T_{ZT}$' are obtained by calculating the forward kinematics for the AESOP and Zeus robots respectively. 'P' is a random point chosen for the registration. Location of 'P' should be easily accessible by both the robots for proper registration. Now to obtain '$T_{AP}$', the camera 'C' is placed at the position 'P' and the forward kinematics is calculated. The tool 'T' is placed at position 'P' and the forward kinematics is calculated to obtain '$T_{zp}$'.

Now to obtain '$T_{AZ}$', the transformation between 'A' to 'P' is multiplied with the transformation between 'P' to 'Z', which is the inverse of the transformation between 'Z' to 'P'. Therefore, $$T_{AZ}=T_{AP}*T_{ZP}^{-1} \qquad \text{Equation 13}$$

Now, the transformation between 'A' and 'T will be the transformation between 'A' and 'Z' multiplied by the transformation between 'Z' and 'T.
Therefore, $$T_{AT}=T_{AZ}*T_{ZT} \qquad \text{Equation 14}$$

To calculate the position of the tool 'T' with respect to the position of the camera 'C', the transformation between 'C' and 'T may be obtained, which can be represented by '$T_{CT}$'. The transformation '$T_{CT}$' can be obtained by multiplying the transformation between 'T' and 'A' to the transformation between 'A' and 'C'. However, the transformation between 'T' and 'A' is the inverse of the transformation '$T_{AT}$'. Therefore, $$T_{CT}=T_{AT}^{-1}*T_{AC} \qquad \text{Equation 15}$$

Using the above equation, the position of the tool with respect to the position of the camera can be calculated. The position of the tool with respect to the camera may be used to find out if the tool is in the view or not and an appropriate action may be taken by the software to position the camera so that the tool is in the view.

Zoom mode is the first control mode for the camera. In this mode the position of the tool and the position of the camera are tracked. Further, the position of the tool with respect to the camera is calculated following the procedure discussed above. Now the position of the camera, 'C', the position of the tool with respect to the camera, '$T_c$', and the position of the trocar through which the camera is placed, '$T_r$' have been calculated.

The vector from 'T$_r$' to 'C' may be calculated as:

$$V_{RC} = C - T_r \qquad \text{Equation 16}$$

The vector from 'C' to 'T', 'V$_{CT}$' will be equal to 'T$_c$' because 'V$_{CT}$' is the position of the tool with respect to the camera.

Now the angle between vectors 'V$_{RC}$' and 'V$_{CT}$' may be calculated using the following formula.

$$\theta = \cos^{-1}\left(\frac{\vec{V_{RC}} \cdot \vec{V_{CT}}}{|V_{RC}| * |V_{CT}|}\right) \qquad \text{Equation 17}$$

FIG. 22 is a diagram showing the field of view of the camera and the tool in the field of view. θ is the calculated angle and the V$_{RC}$ is the vector between the trocar and the camera position. The field of view of the camera 2210, from the center, has been calculated as 35°. If the value of θ, calculated using the above equation is less than 35°, which means the tool 2220 is in the view of the camera, but if it is greater than 35°, it means the tool 2220 is out of view.

The angle, θ, may be calculated using the above formula and if θ is greater than 35°, the linear joint of the AESOP Robot may be moved up, as a result, the camera moves up. This is done in steps of 2 cm every time until the angle θ is less than a first threshold angle such as 35°. This way, if the tool goes out of view, the camera autonomously positions itself so that the tool comes back to view.

If the angle θ is close to 0°, it means the tool is in the center of the camera view. So, whenever the angle falls below a second threshold angle such as 15°, the linear joint of the AESOP Robot may be moved down, as a result the camera zooms into the scene and the tool appears to be closer. This could be useful when the user is performing a delicate task and needs a clearer view of the scene. When the camera is zooming in, the system is programmed to stop zooming in further, if the distance between the tool and the camera is less than a threshold amount such as 2 cm. Limiting the distance between the tool and the camera prevents the camera from hitting the tool and damaging the lens. Performing tasks can also be difficult if the camera is very close to the tool. The threshold distance of 2 cm was found to be a comfortable threshold. When the camera zooms out to get the tool back in view, the camera might slide out of the trocar point. In order to avoid the camera sliding out of the trocar point, the distance between the camera and the trocar is calculated before zooming out. If the distance between the camera and trocar point is less than a distance threshold, such as 1 cm, the camera may be programmed to stop zooming out.

The follow mode is the second mode of control for the camera positioning. In the follow mode, the camera is positioned so that the tool is always in the center of the view. The position of 'T' with respect to 'A' can be obtained from the transformation 'T$_{AT}$', which was discussed previously. In addition, the position of the trocar, 'T$_r$' with respect to 'A' has also been calculated. Now as the tool is moving, a first point which lies along the line between and 'A' and is one fourth the distance between 'T$_r$' and 'A' from 'T,' is calculated. The first point is given to the inverse kinematics algorithm of the AESOP Robot to position the camera at the first point. When the camera reaches the first point, the camera's position is along the line between the trocar and the tool and since it passes through the trocar, its points along the same line, as a result of which the camera has the tool in the view. This is done repetitively and thus the camera may follow the tool wherever the tool goes. Various examples can be seen in FIGS. 23a-d. In each of these figures, the camera is denoted by 2310, the tool is denoted by 2312, and the trocar is denoted by 2314. The calculated position is one fourth the distance away from T$_R$ along the line from T$_R$ to T.

When the camera control is in follow mode, the continuous motion of the camera can cause motion sickness to the user and it can also be very irritating. In order to avoid motion sickness, the speeds of each joint of the AESOP Robot are set to low values. Moreover, the Galil Motion Controller does not allow motion commands to be sent while the robot is moving. In order to avoid conflict, the program may check if the robot is moving or not and will send the motion commands only when the robot is not moving. Because of the delay in sending commands, the robot moves at very slow speeds and therefore, the response of the camera might be sluggish. The speeds of the joints of the AESOP Robot may be adjusted to improve the response, but care should be taken not to make the movement too fast.

The inverse kinematics algorithm of the AESOP robot might not be very accurate. Due to the accuracy, the tool may not be exactly in the center of the view, but the tool should not leave the view. The inaccuracy of the inverse kinematics also means that it is possible that the camera might slide out of the trocar point when the tool comes close to the trocar. In order to avoid sliding of the camera, the motion commands are not sent to the robot if the camera is less than a threshold distance, such as 1 cm, away from the trocar point.

As described above, the system may support autonomous zoom control of the laparoscopic camera. The AESOP 1000 robot, which may hold the laparoscopic camera, can be configured to adjust the zoom level of the camera by moving the camera up or down based on the position of the tools. The camera may zoom out if the tool is at the edge of the view and may zoom in if the tool is in the center of the view. The angle between the position of the tool and the camera may be calculated and compared to two thresholds. The outer threshold may be 35° and if the angle is greater than this threshold, the camera may zoom out. The inner threshold is 15° and if the angle is less than the inner threshold, the camera may zoom in. Whenever the angle becomes less than the inner threshold, the distance between the camera and the tool is checked. If the distance is less than a first limit, such as 2 cm, the camera is not zoomed in further. This check avoids the camera being zoomed in too close to the tool. Whenever the angle is greater than the outer limit, the distance between the camera and the trocar point is checked. If the distance is less than a second limit, such as 1 cm, the camera is not zoomed out further. The second check avoids the camera from sliding out of the trocar.

FIGS. 24a-c shows three images of the camera view in autonomous zoom mode. FIG. 24a shows the camera zoomed in because the tool 2410 is in the center of the view. FIGS. 24b and c, show the camera zoomed out because the tool 2410 is close to the edge of the view. The difference in the zoom level can be inferred by observing the size of the squares in each picture. The size of the squares in FIG. 24a picture is larger than the size in FIGS. 24b and c.

In addition, the system may be configured in an autonomous follow mode in which the camera follows the tool and keeps the tool in the center of the view. In the autonomous follow mode, the position of the tool may be used to calculate the position of the camera so that the tool is in the center of the view. FIGS. 25a-c shows images of the camera view in the zoom mode. In FIG. 35a, the tool 2510 is in the center. In FIG. 25b, the tool 2510 is moved to the left edge of the scene and the camera followed the tool 2510 (Note that the left side of the picture shows the left edge of the paper). In FIG. 25c, the tool 2510 is moved to the top right corner of the scene and the camera followed the tool 2510 (Note that the top right side of the picture shows the top corner of the paper).

As such, both features discussed have been implemented using the Zeus Surgical System apart from restoring the tele-operation. Adding these features allows the surgeons to concentrate on their tasks and the system takes care of placing the camera in the optimum position.

Although the camera may always follow the tool and never loses track of the tool, the kinematics of the AESOP robot may not be accurate enough. The D-H Parameters of the AESOP 1000 robot were measured using vernier calipers to the best possible accuracy for testing, but this technique may not be accurate enough for surgical automation. Hence the accurate D-H Parameters of the robots may be obtained for better accuracy. One possible way to calculate the D-H parameters more accurately is by using optimization algorithms to calculate the D-H parameters. Moreover, passive joints on the robot increase the difficulty in calculating the inverse kinematics.

It should be noted that the robots used in testing these concepts, Zeus and AESOP are designed for tele-operation and not automation. In tele-operation, since the surgeon is the one controlling the robot, it is not as necessary for the kinematics to be very accurate. One major contributor for inaccuracies in the Zeus and AESOP is the mountings of the robot. The mountings are not rigid and hence the robots may lean when the arms are extended and thus may change the position and orientation of the base, which is very important for kinematics of the robot. Hence, for surgical automation, the robots may be designed specifically for automation, without passive joints and with better mountings, and that will lead to better accuracy.

While the system was tested to position of the camera based on the position of one tool. The system could be extended to accommodate two arms. One of the control strategies with two arms may be to follow the mid-point of the two arms and adjust the zoom so that both the tools are in the view. This way the system can combine both the Zoom mode and the Follow mode. If the tools are far apart, the camera may zoom out and may center to the mid-point of the two tools. If the tools are very close to each other, the camera may zoom in, giving a better view of the tools.

Since the position of the tools are being tracked, the system may implement virtual fixtures. Using virtual fixtures, 'No-Fly' zones can be defined in the patient's body which will prevent the tools from entering sensitive areas of the patient's body without the surgeon's knowledge. Further, when the camera is at its maximum zoomed out position, if the surgeon tries to move the tool out of the view at that point, the motion can be restricted and the surgeon can be informed that it is unsafe to move out of the view.

Since the tools and the camera are being registered with respect to one another, the surgeon can define the 'No-Fly' zones using one tool. The 'No-Fly' zones can be transformed to the other tools using the registrations to prevent the other tools from entering the sensitive areas. As such, the surgeon does not have to define the zones for each tool separately.

One of the joints which were not used during testing on the AESOP robot is the 'Roll' joint, which controls the camera roll. Using the roll joint, the camera can be rotated along the camera's viewing. The rolling motion of the camera will rotate the view and hence affect the control of the tools using the master controller. For example, the camera is in its normal position and there is no roll, then if the surgeon moves the master controller to the left, the tool may move to the left. Then, if the camera is rolled 1800, all the motions will be reversed and if the surgeon moves the controller to the left, the tool moves to the right in the camera view. If the 'Roll' joint is tracked, it is possible to provide the surgeon with Augmented Reality Cues suggesting which are the X, Y and Z axes of the tool with respect to the camera. It is also possible to transform the motion of the tools based on the roll of the camera so that the tools moves in the same direction (in the camera view) as the controller is moved no matter what the orientation of the camera. Adjusting the motion or providing augmented reality cues can possibly avoid confusion during the surgery.

Using the control described herein, it is possible to automate certain surgical tasks like suturing, knot tying, etc. Using the techniques of tele-operation and full inverse kinematic solutions, new algorithms can be developed to automate the surgical tasks.

Figure 26:
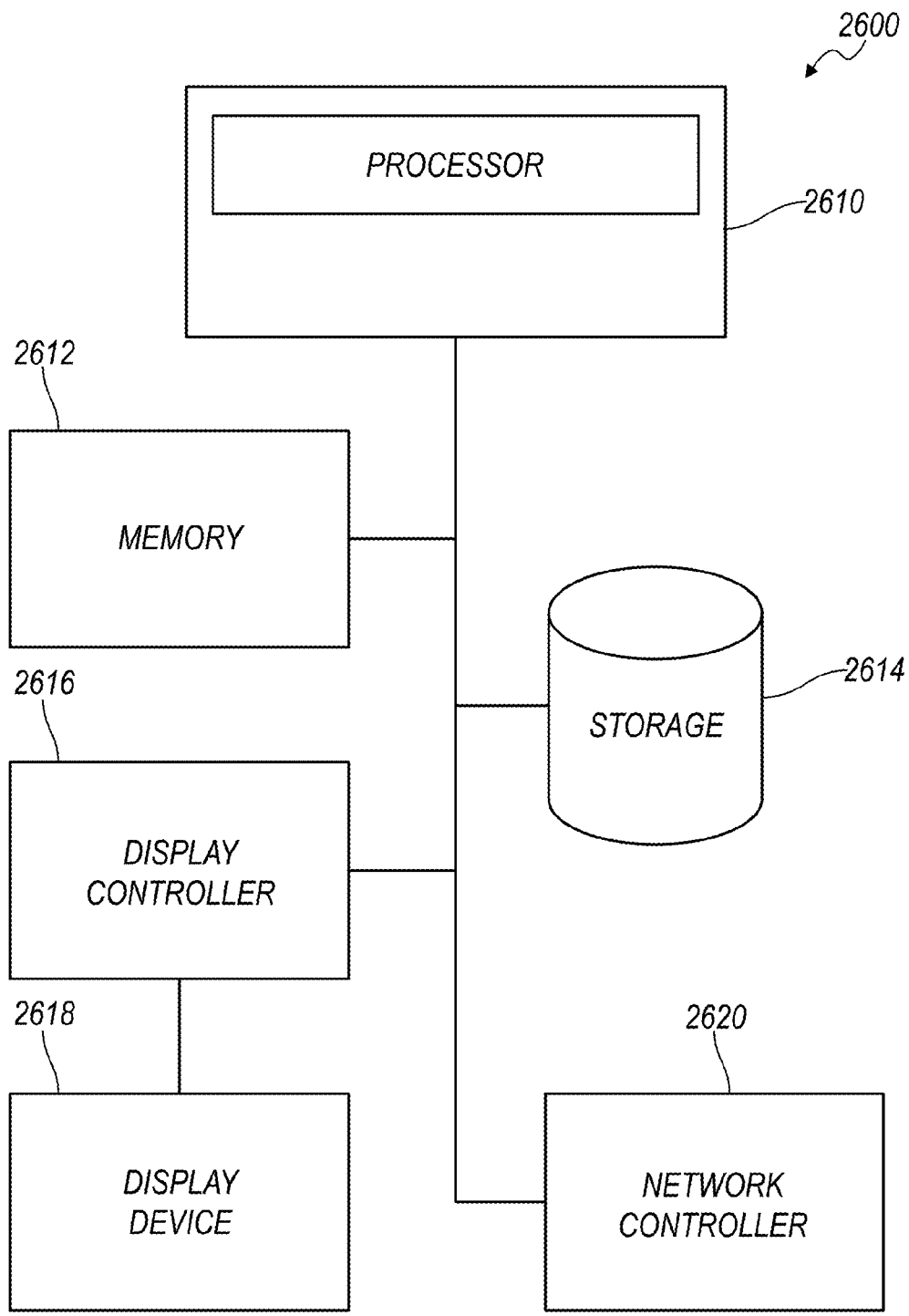
FIG. 26 is a schematic view of a computer system for implementing the methods described herein.

Any of the methods described may be implemented and controlled with one or more computer systems. If implemented in multiple computer systems the code may be distributed and interface via application programming interfaces. Further, each method may be implemented on one or more computers. One exemplary computer system is provided in FIG. 26. The computer system 2600 includes a processor 2610 for executing instructions such as those described in the methods discussed above. The instructions may be stored in a computer readable medium such as memory 2612 or a storage device 2614, for example a disk drive, CD, or DVD. The computer may include a display controller 2616 responsive to instructions to generate a textual or graphical display on a display device 2618, for example a computer monitor. In addition, the processor 2610 may communicate with a network controller 2620 to communicate data or instructions to other systems, for example other general computer systems. The network controller 2620 may communicate over Ethernet or other known protocols to distribute processing or provide remote access to information over a variety of network topologies, including local area networks, wide area networks, the internet, or other commonly used network topologies.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

Further the methods described herein may be embodied in a computer-readable medium. The term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

As a person skilled in the art will readily appreciate, the above description is meant as an illustration of the principles of this application. This description is not intended to limit the scope or application of the claim in that the invention is susceptible to modification, variation and change, without departing from spirit of this application, as defined in the following claims.

We claim:

1. A system for autonomous camera control, the system comprising:
   a first robot having a surgical tool mounted as an end effector;
   a second robot having a camera mounted as an end effector;
   a controller for manipulating the second robot, wherein the controller stores a first kinematic model for the first robot and a second kinematic model for the second robot, the controller being configured to automatically manipulate the second robot to position the camera based on the second kinematic model and an expected position of the surgical tool according the first kinematic model of the first robot, wherein the controller is configured to identify a threshold angle from a viewing axis of the camera, calculate a tool angle from the viewing axis of the camera, moving camera further away from the tool if the tool angle is greater than the threshold angle.

2. The system of claim 1, wherein the tool angle is calculated according to the relationship:

$$\theta = \cos^{-1}\left(\frac{\vec{V}_{RC} \cdot \vec{V}_{CT}}{|V_{RC}| * |V_{CT}|}\right)$$

where $V_{RC}$ is the vector between a trocar and the camera position, $V_{CT}$ is the vector between the camera and the tool, and $\theta$ is the tool angle.

3. The system of claim 1, wherein the controller is configured to calculate a distance of the camera from a point within a trocar, the controller preventing the camera from adjusting the camera backward based on the threshold angle when the distance of the camera from the point within the trocar is less than a threshold distance.

4. The system of claim 1, wherein the controller is in communication with an input device for control of the first robot and a display for providing an image from the camera, the system being configured to maintain the relation between the image and the input device.

5. The system of claim 1, wherein the controller tracks roll of the camera and provide cues to the surgeon suggesting the direction of motion of the surgical tool.

6. The system of claim 1, wherein the controller is configured to maintain a relationship between the camera and the tool based on the first and second kinematic model.

7. The system of claim 1, wherein the controller is configured to position the camera so that the tool is in the center of the view.

8. The system of claim 1, wherein the controller calculates a first point which is on a line between a point within a trocar and the surgical tool.

9. The system of claim 8, wherein the first point is located a distance away from the point within the trocar that is about one fourth of a distance from the point within the trocar to the surgical tool.

10. The system of claim 1, wherein the controller positions the camera based on the relationship:

$$T_{CT} = T_{AT}^{-1} * T_{AC}$$

where $T_{CT}$ is the transform from the camera to the tool, $T_{AT}$ is the transform from the origin of the second robot to the tool, $T_{AC}$ is the transform from the origin of the second robot to the camera.

11. The system of claim 1, wherein the first robot is one robot of a plurality of robots, each robot of the plurality of robots having a surgical tool of a plurality of surgical tools, and controller is configured to position the camera such that the mid-point of the plurality surgical tools is in the center of the field of view of the camera.

12. The system of claim 1, wherein the controller is configured to define a zone such that the first robot will not be allowed to enter the zone.

13. The system according to claim 12, wherein the controller is configured to determine the motion of the second robot to avoid entering the zone that was defined with respect to the first robot.

14. A system for autonomous camera control, the system comprising:
   a first robot having a surgical tool mounted as an end effector;
   a second robot having a camera mounted as an end effector;
   a controller for manipulating the second robot, wherein the controller stores a first kinematic model for the first robot and a second kinematic model for the second robot, the controller being configured to automatically manipulate the second robot to position the camera based on the second kinematic model and an expected position of the surgical tool according the first kinematic model of the first robot, wherein the controller is configured to identify a threshold angle from a viewing axis of the camera, calculate a tool angle from the viewing axis of the camera, moving camera closer to the surgical tool if the surgical tool angle is less than the threshold angle.

15. The system of claim 14, wherein the controller is configured to calculate a distance of the camera from the surgical tool, the controller preventing the camera from adjusting the camera toward the surgical tool based on the threshold angle when the distance of the camera from the surgical tool is less than a threshold distance.

16. A method for autonomous camera control, the method comprising:
   storing a first kinematic model for a first robot and a second kinematic model for a second robot;
   identifying a threshold angle from a viewing axis of the camera, calculating a tool angle from the viewing axis of the camera, moving camera further away from the tool if the tool angle is greater than the threshold angle;
   automatically manipulating the second robot to position a camera based on the second kinematic model and an expected position of a surgical tool mounted on the first robot according the first kinematic model of the first robot.

17. The method of claim 16, further comprising identifying a threshold angle from a viewing axis of the camera, calculating a tool angle from the viewing axis of the camera, and moving camera closer to the surgical tool if the surgical tool angle is less than the threshold angle.

18. The method of claim 16, further comprising calculating a first point which is on a line between a point within a trocar and the surgical tool, wherein the first point is located a distance away from the point within the trocar that is about one fourth of a distance from the point within the trocar to the surgical tool, and moving the camera to the first point.

* * * * *